(12) United States Patent
Zdeblick et al.

(10) Patent No.: US 8,372,149 B2
(45) Date of Patent: Feb. 12, 2013

(54) ARTIFICAL DISC IMPLANT

(75) Inventors: Thomas A. Zdeblick, Middleton, WI (US); William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 193 days.

(21) Appl. No.: 12/786,030

(22) Filed: May 24, 2010

(65) Prior Publication Data

US 2010/0234957 A1    Sep. 16, 2010

Related U.S. Application Data

(63) Continuation of application No. 12/382,549, filed on Mar. 18, 2009, now abandoned.

(51) Int. Cl.
*A61F 2/44*      (2006.01)

(52) U.S. Cl. ..................................... 623/17.15

(58) Field of Classification Search ..... 623/17.11–17.16
See application file for complete search history.

(56) References Cited

U.S. PATENT DOCUMENTS

| 4,349,921 A | * | 9/1982 | Kuntz ........................ 623/17.16 |
| 5,888,226 A | * | 3/1999 | Rogozinski ................ 623/17.16 |

* cited by examiner

*Primary Examiner* — David Isabella
*Assistant Examiner* — Ann Schillinger

(57) ABSTRACT

An artificial disc implant includes an upper shell, a lower shell, and a spacer therebetween. The spacer preferably has properties similar to that of a natural spinal disc, while the upper and lower shells form a rigid interface between the implant and the adjacent vertebral bodies. The upper and lower shells can be configured to prevent expulsion of the spacer from the disc space. The implant upper and lower shells may further be configured into partially cylindrical shapes for ease of insertion through an insertion tube as presently known for interbody fusion devices. The devices may further be configured for insertion through a double-barreled insertion tube. Methods and instruments for inserting an artificial disc implant are also provided.

13 Claims, 19 Drawing Sheets

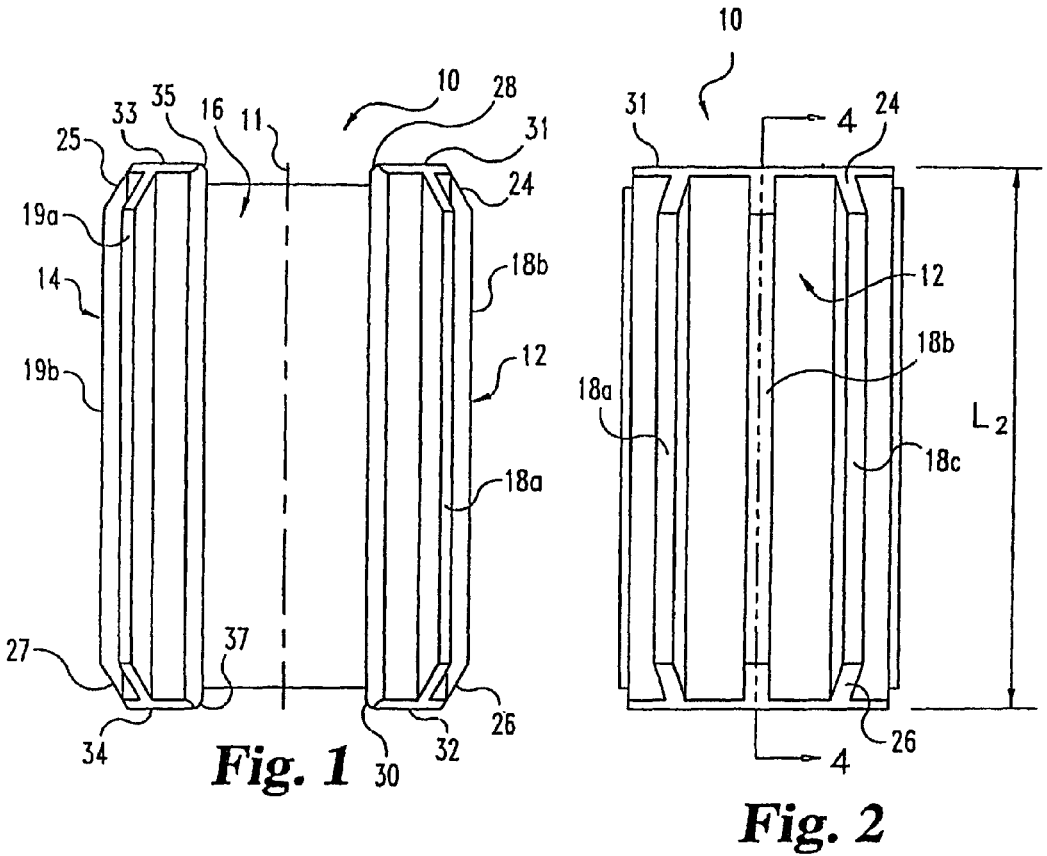
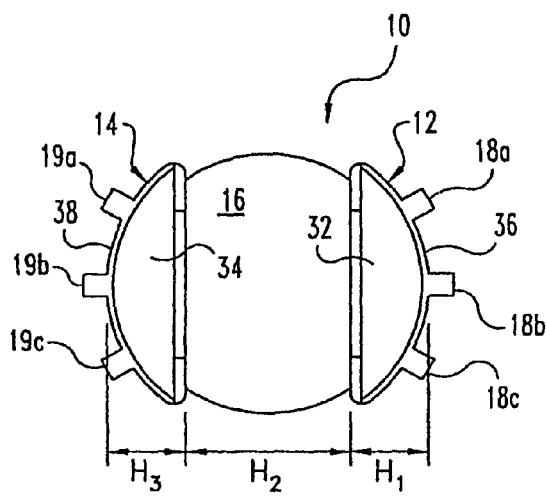

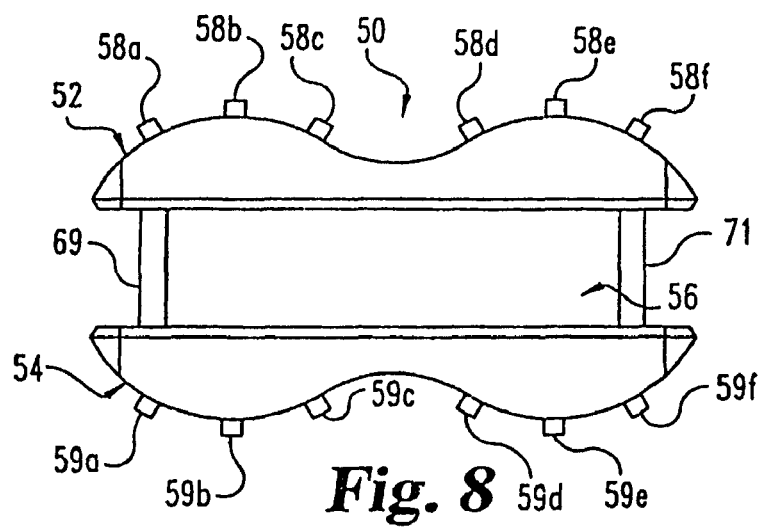
Fig. 8
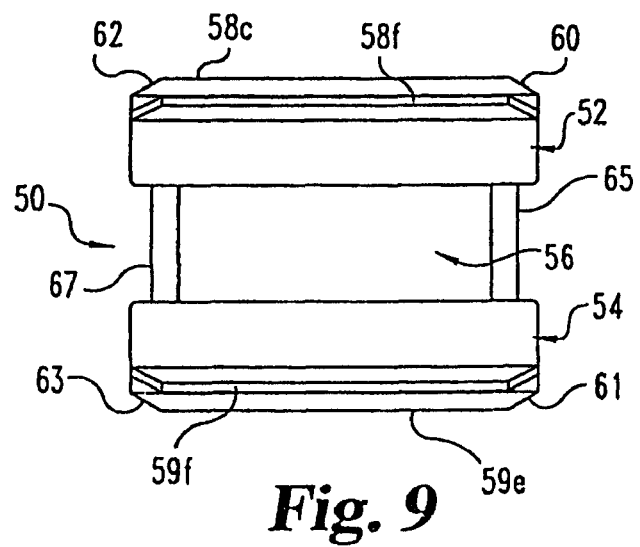
Fig. 9
Fig. 10

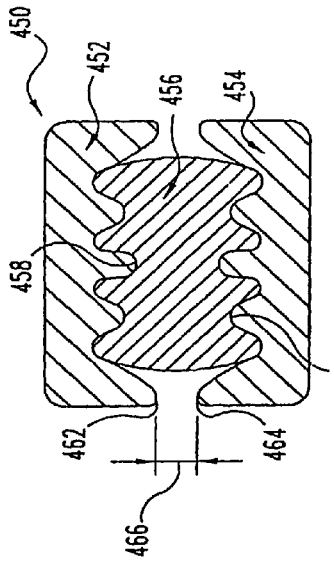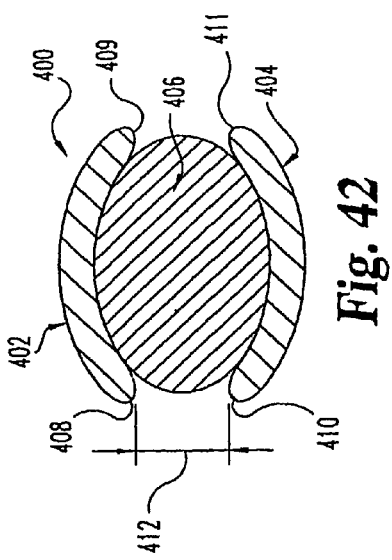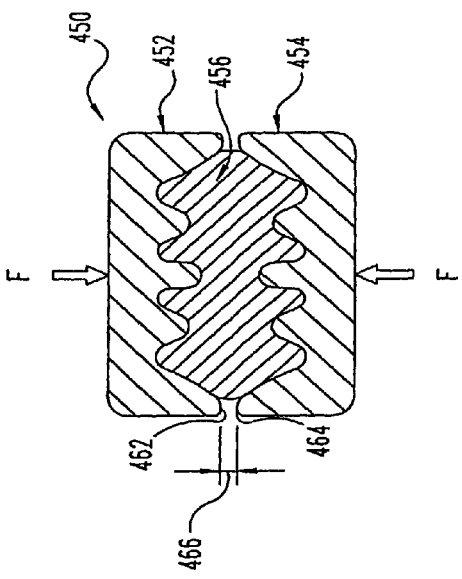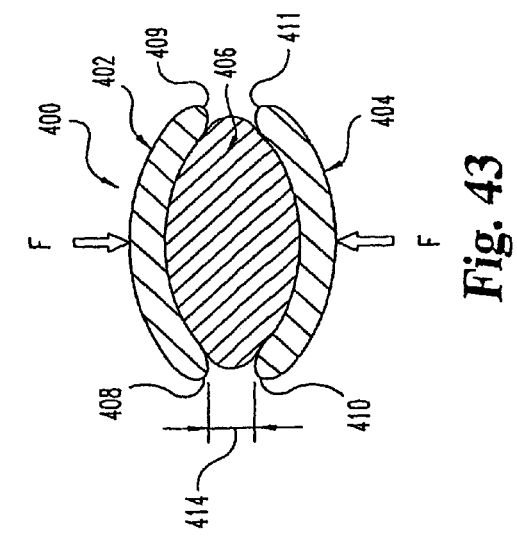

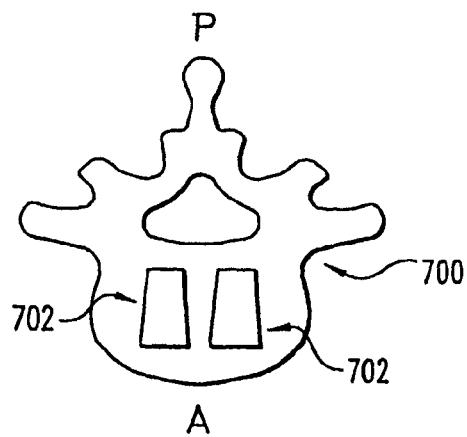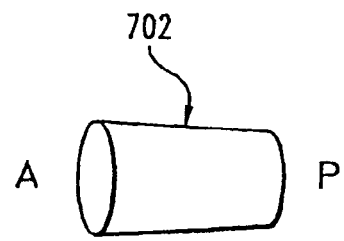
*Fig. 49a*  *Fig. 49b*
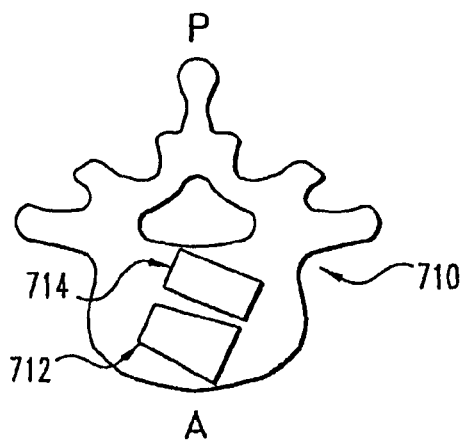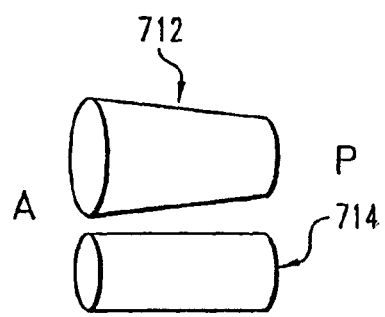
*Fig. 50a*  *Fig. 50b*
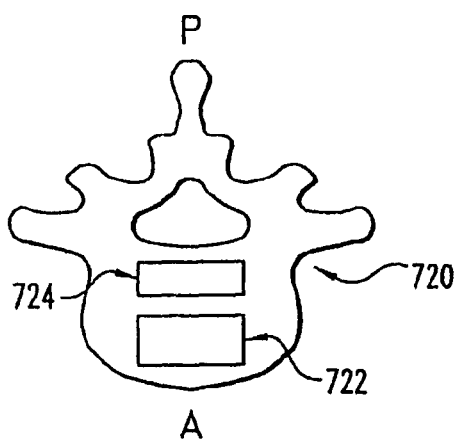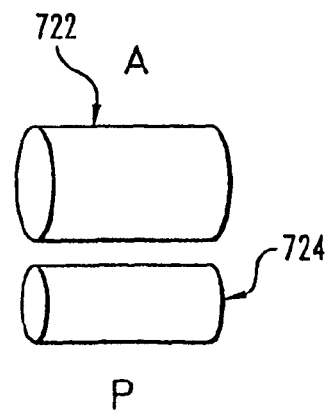
*Fig. 51a*  *Fig. 51b*

ARTIFICAL DISC IMPLANT

CROSS-REFERENCE TO RELATED APPLICATIONS:

This application is a continuation of copending U.S. patent application Ser. No. 12/382,549 filed Mar. 18, 2009 which is a continuation of U.S. patent application Ser. No. 11/064,185 filed on Feb. 23, 2005 which is a divisional application of U.S. patent application Ser. No. 10/085,872 filed on Feb. 28, 2002 which is a divisional of U.S. patent application Ser. No. 09/586,308 filed on Jun. 2, 2000 which claims the benefit of the filing date of U.S. Provisional Application Ser. No. 60/137,586 filed Jun. 4, 1999. The referenced applications are incorporated herein by reference in their entirety.

BACKGROUND

The present invention relates to artificial disc replacement devices. Previous attempts at artificial disc replacement have not received wide spread acceptance because of a number of problems. In some attempts at disc replacement, a flexible artificial disc is placed within the intervertebral disc space without any anchoring system, with the expectation that the artificial disc will remain in place in the disc space based on contact with the ligaments of the disc annulus and/or the vertebral bodies. With this approach there remains an unacceptable rate of protrusion of the artificial disc from the disc space. Further, over time the artificial disc may wear against the adjacent vertebral endplates, generating wear particles in the disc space and creating the risk of failure of the artificial disc.

Alternative designs have provided a rigid interface between the vertebral end plates and a shock absorbing compound disposed in the disc space between the rigid interfaces. The drawbacks of many of these prior devices are that they require extensive disc space preparation prior to placement. Other attempts at disc replacement provide a device having multiple components that must be positioned in the disc space.

The present invention is directed to providing improved artificial disc replacement implants directed to solving a number of the problems and disadvantages of the previous attempts at disc replacement.

SUMMARY

The present invention provides an improved artificial disc implant for replacing the spinal disc between two vertebrae of the spine. The implant comprises an upper shell, a lower shell and a spacer or insert therebetween. Preferably the implant is insertable as a single unit into the disc apace between two adjacent vertebral bodies. The shells may be made from any suitable bio-compatible material.

According to one aspect of the invention, the upper and lower shells each include a pair of interconnected cylindrical lobes. In one form, the upper and lower shells are partially cylindrical.

Further, the present invention contemplates insertion into the disc space via tubular instruments presently used for interbody fusion procedures. Thus, the instrumentation utilized to perform current interbody fusion techniques may also serve a dual function for disc replacement procedures.

In another aspect of the present invention, there is provided an upper and lower shell for engagement with the vertebral bone of the adjacent vertebral bodies. The upper and lower shells each have anchoring means to prevent movement in at least one direction. In one form, the anchoring means are ribs that prevent rotation of the shell in the disc space. In another form, each shell includes a flange extending therefrom. Each flange has an aperture extending therethrough receiving a bone screw to engage the shell to the adjacent vertebra.

Another aspect of the present invention, there is provided mating surfaces between the upper and lower shells to restrict the transmission of shear forces through the spacer disposed between the upper and lower shells. In one form, the mating surfaces are provided by multiple projections and that are positionable in corresponding recesses to restrict movement in multiple directions while permitting compression of the spacer disposed between the upper and lower shells.

In still a further aspect of the present invention, shells for contacting the upper and lower vertebral end plates are provided to anchor the device, and multiple spacer shapes are provided between the shells to permit insertion from a variety of approaches to the disc space, including anterior, posterior, lateral, anterior-lateral, and posterior-lateral approaches. The multiple spacer shapes are configured to address a variety of angulations between the adjacent vertebrae. Various instruments and methods for insertion one or more artificial disc implants to the disc space from a variety approaches are also provided.

In yet another aspect of the present invention, the spacer includes two interconnected cylindrical portions and the upper and lower shells have cavities shaped to securely retain the spacer therebetween.

In a further aspect of the invention, the spacer is inserted between the upper and lower shells. The sidewalls of the spacer are truncated adjacent the gap between the upper and lower shells to limit potential impingement of the material between the upper and lower shells as the spacer is compressed.

In yet another aspect of the preferred invention, each of the upper and lower shells includes a substantially cylindrical bone engagement surface for contact with a substantially cylindrical bone opening in the vertebral end plates. Preferably, the shells include structure to engage the bone beyond the opening to limit movement of the shells in at least one direction.

According to another aspect of the present invention, the implant includes a spacer formed from a hydrogel substance. In one method of inserting the implant according to the present invention, the hydrogel is at least slightly dehydrated thereby reducing the height of the implant for insertion. Once inserted, the hydrogel can be hydrated to increase the overall height of the implant to the desired working height.

These and other aspects, features, embodiments, forms, and advantages of the invention will become apparent from the following description of the illustrated embodiments.

BRIEF DESCRIPTION OF THE DRAWINGS

FIG. 1 is a side view of an artificial disc implant according to the present invention.

FIG. 2 is a side view of the artificial disc implant of FIG. 1 rotated 90 degrees about its axis.

FIG. 3 is an end view of the implant of FIG. 1.

FIG. 8 is an end view of the implant of FIG. 7.

FIG. 9 is a side view of the implant of FIG. 7.

FIG. 10 is an end view of a shell comprising a portion of the implant of FIG. 7.

FIG. 36(*b*) is a perspective view of the spacer shown in cross-section in FIG. 36(*a*).

FIG. 42 is a cross-sectional view of the relaxed state of a substantially cylindrical artificial disc implant according to the present invention having a spacer disposed between upper and lower partial cylindrical shells.

FIG. 43 shows the implant of FIG. 42 in a compressed state with the upper and lower shells positioned closer to each other.

FIG. 44 is a cross-sectional view of a relaxed state of an artificial disc replacement implant according to the present invention having upper and lower shells with substantially planar bone contacting surfaces and a spacer disposed therebetween.

FIG. 45 shows the implant of FIG. 44 in a compressed state.

FIGS. 49(*a*) and 49(*b*) illustrate an implant having spacers shaped according to the present invention for insertion into the disc space from an anterior approach.

FIGS. 50(*a*) and 50(*b*) illustrate an implant having spacers shaped according to the present invention for insertion into the disc space from an antero-lateral approach.

FIGS. 51(*a*) and 51(*b*) illustrate an implant having spacers shaped according to the present invention for insertion into the disc space from a substantially lateral approach.

DESCRIPTION OF THE ILLUSTRATED EMBODIMENTS

Figure 4:
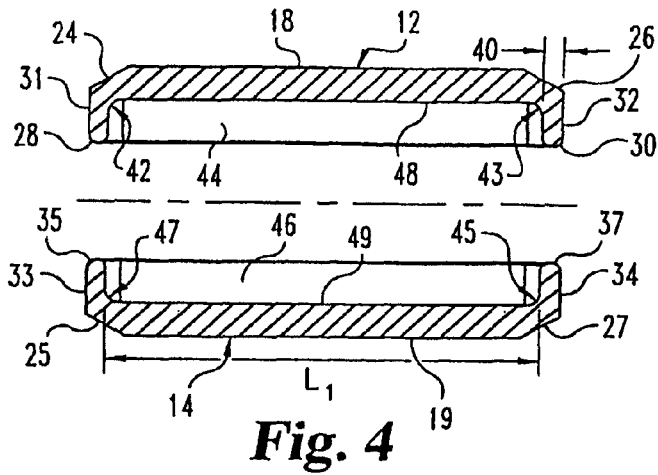
FIG. 4 is a partial cross-sectional view of the implant of FIG. 2 taken along line 4-4 with spacer removed.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and any such further applications of the principles of the invention as illustrated therein are contemplated as would normally occur to one skilled in the art to which the invention relates.

The present invention is directed to improved artificial disc implants used to replace the spinal disc in an animal subject. In one embodiment, the invention contemplates an insert or spacer made from elastomer or hydrogel having properties of elasticity similar to or equivalent to a natural spinal disc. The spacer or insert is disposed between, but preferably not interconnected with, an upper shell and a lower shell, each of which contact and/or engage an adjacent vertebral body.

Referring now to FIGS. 1-6, there is shown a first preferred embodiment of an artificial disc implant according to one aspect of the invention. More specifically, implant 10 includes an upper shell 12, a lower shell 14, and an intermediate insert or spacer 16. Spacer 16 preferably has elastic properties substantially equivalent to the natural elastic properties of the human body's intervertebral disc. In the illustrated embodiment, upper shell 12 and lower shell 14 are substantially identical; however, it is contemplated that there could be differences between the upper and lower shells without deviating from the spirit and scope of the present invention. The shells may be formed of any suitable bio-compatible material. For example, but without limitation, the shells may be composed of stainless steel, titanium, polymers, carbon fiber, shape memory alloys, or porous material. In the description that follows, the description of upper shell 12 applies with like effect to lower shell 14.

In the illustrated embodiment, upper shell 12 is partially cylindrical and includes a bone contacting surface 36 and lower shell 14 is partially cylindrical and includes a bone contacting surface 14, each of which is substantially arcuate and extends about longitudinal axis 11 to form a substantially cylindrical surface. Bone contacting surface 36 is interrupted by a number of ribs 18a, 18b and 18c, collectively referred to as ribs 18, and bone contacting surface 38 is interrupted by a number of ribs 19a, 19b and 19c, collectively referred to as ribs 19. In the illustrated embodiment, three such retention ribs 18 and 19 are provided on each shell; however, a fewer number or greater number of ribs are also contemplated. While a straight uninterrupted rib 18, 19 is shown in the preferred embodiment, it is contemplated that other retention mechanisms such as barbs, interruptions, scales, etc., may be utilized to assist in retention and engagement of the upper and lower shells with its adjacent vertebral bodies. Ribs 18 and 19 further resist rotation of implant 10 about its longitudinal axis 11 in the disc space.

Figure 5:
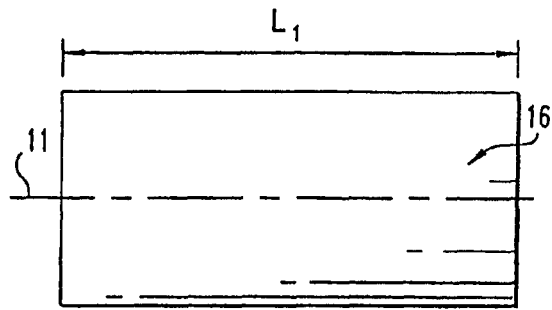
FIG. 5 is a side view of a spacer for the implant of FIG. 1.
Figure 6:
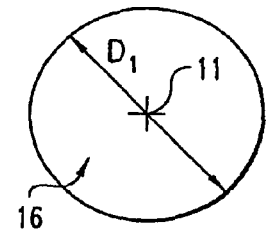
FIG. 6 is an end view of the spacer of FIG. 5.

As shown in FIG. 5 spacer 16 has a length L1 along longitudinal axis 11, and as shown in FIG. 6 has a cylindrical shape extending along longitudinal axis 11 with a diameter D1. Referring now to FIG. 2 upper shell 12 lower shell 14 each have a length L2 that is greater than spacer 16 length L1. Upper shell 12 and lower shell 14 thus extend substantially beyond the spacer 16 length to form overhanging end portions 28 and 30 and overhanging end portions 35 and 37, respectively, as shown in FIGS. 1 and 4. Overhanging end portion 30 of upper shell 12 includes an end wall 32, and a similar end wall 31 is included with overhanging end portion 28. Overhanging end portion 37 of lower shell 14 includes an end wall 34, and a similar end wall 33 is included with overhanging portion 35. Upper shell 12 includes a tapered portion 26 extending from end wall 32 and through ribs 18 and a corresponding tapered portion 24 on the opposite end. Lower shell 14 includes a tapered portion 27 extending from end wall 34 and through ribs 19 and a corresponding tapered portion 25 on the opposite end. The tapered portions may assist in easing insertion of the device through an insertion apparatus, such as a sleeve, and into the disc space.

Referring to FIG. 4, upper shell 12 includes the combination of partially cylindrical interior bearing wall 48 and end walls 31 and 32 to create an interior cavity or chamber 44 adapted to receive at least a portion of spacer 16 therein. Lower shell 14 similarly includes the combination of preferably cylindrical interior bearing wall 49 and end walls 33 and 34 to create an interior cavity or chamber 46 adapted to receive at least a portion of spacer 16 therein. The combination of interior chambers 44 and 46 cooperate to receive the cylindrically shaped spacer 16 and restrain movement of spacer 16 in shells 12, 14. In the illustrated embodiment, the junctions between interior bearing wall 48 and end walls 31, 32 are curved to form an arcuate surfaces 42, 43 respectively, to limit abrupt changes in the surface configuration that might be encountered by the spacer 16. Lower shell 14 similarly includes arcuate surfaces 47, 45 formed at the junction of bearing wall 49 and end walls 33, 34, respectively.

As shown in FIG. 3, implant 10 has an overall height in the disc space measured from upper bone contacting surface 36 to lower bone contacting surface 38. Preferably, upper shell 12 has a height H1 between bone contacting surface 36 and its lower edge, lower shell 14 has a height H3 between bone contacting surface 38 and its upper edge, and spacer 16 comprises the remaining portion of the device height with a height H2 extending between the edges of upper shell 12 and lower shell 14. It will be understood that as load is applied to the upper and lower shells, H1 and H3 will remain substantially constant while H2 will vary based on the applied load and the properties of spacer 16. Furthermore, in a preferred embodiment H2 is substantially greater than either H1 or H3, and H1 and H3 are the same. In a further embodiment, greater than fifty percent of the spacer height is unconstrained by the upper or lower shells permitting substantial movement in the spacer to absorb compressive loads applied to implant 10 while preserving disc motion.

The three components of top shell 12, spacer 16, and lower shell 14 are preferably inserted into an intervertebral disc space as a single unit. The upper and lower shells may be urged towards one another to compress spacer 16. In a compressed condition, the entire implant may be loaded into a delivery tube or sleeve which will maintain at least a portion of the compression during insertion. The entire implant may then be positioned adjacent the disc space and forcibly urged into the disc space by pushing on the trailing portion of each of the shells to urge the leading portion of implant 10 forwardly into the disc space. Preferably, a portion of the disc space has been prepared to create a substantially cylindrical area on the adjacent vertebrae adapted to receive the partially cylindrical portions of upper shell 12 and lower shell 14. Ribs 18, 19 extend beyond the prepared portion of the disc space and embed in adjacent bone, and the bone contacting surfaces 36, 38 are intended to substantially abut the prepared disc space area to inhibit subsidence. More preferably, the prepared portion of the disc space may be limited to the area necessary to receive the length of implant 10 while leaving unprepared portions anterior and posterior of the inserted implant 10. The unprepared anterior and posterior portions of bone may engage the end walls of the upper and lower shells to resist expulsion of implant 10 from the disc space.

In yet a further aspect of the invention, it is contemplated that spacer 16 may be comprised of hydrogels of various forms. It is contemplated that an alternative to or in conjunction with forcibly compressing the entire implant 10, the interior of spacer 16 can be accessed via a syringe, access port, or the like to at least partially dehydrate the hydrogel, thereby assisting in reduction of the height of implant 10 between the upper and lower bone contacting surfaces 36, 38. The reduction in implant height facilitates insertion of implant 10 into the disc space through a smaller opening than could be utilized with an expanded implant 10. Once positioned in the disc space, the hydrogel may be rehydrated to thereby fully expand spacer 16 and restore implant 10 to the desired height in the disc space.

Figure 7:
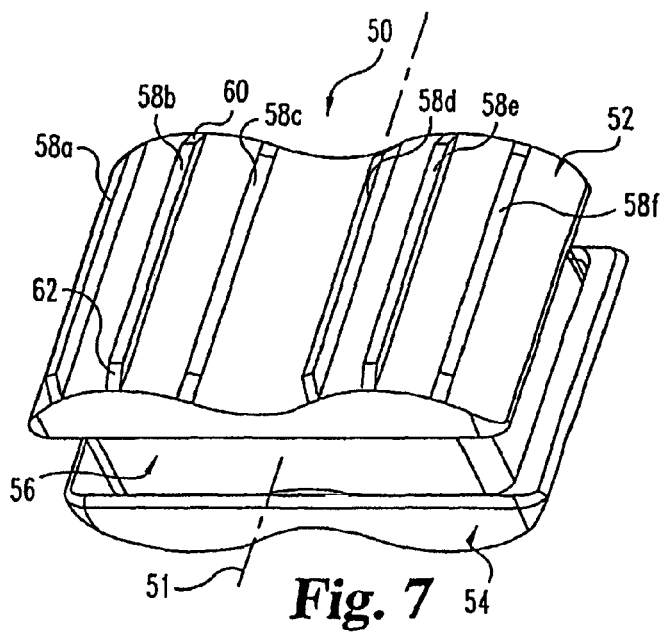
FIG. 7 is a perspective view of another embodiment of an artificial disc implant according to the present invention.
Figure 11:
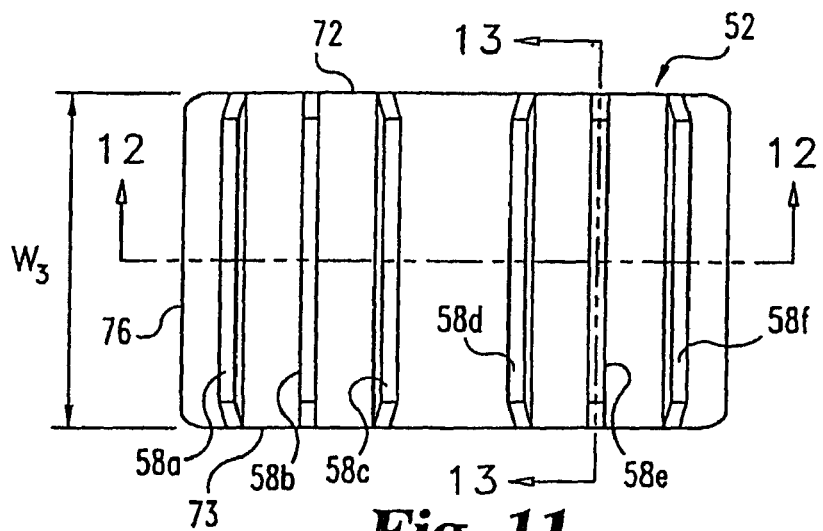
FIG. 11 is a top view of the shell of FIG. 10.

Referring now to FIG. 7, there is shown a further preferred embodiment of an artificial disc implant according to another aspect of the invention. Implant 50 includes an upper shell 52, a lower shell 54, and a spacer 56 disposed therebetween. Implant 50 includes a longitudinal axis 51 extending therethrough. In the illustrated embodiment, upper shell 52 and lower shell 54 are substantially identical; however, it is contemplated that there could be differences between the upper and lower shells without deviating from the spirit and scope of the present invention. In the description that follows, the description of upper shell 12 also applies to lower shell 14.

Referring further to FIGS. 8-9, upper shell 52 includes ribs 58a, 58b, 58c, 58d, 58e, 58f, collectively referred to as ribs 58, and lower shell 54 includes ribs 59a, 59b, 59c, 59d, 59e, 59f, collectively referred to as ribs 59. While straight uninterrupted ribs 58, 59 are shown in the preferred embodiment, it is contemplated that other retention mechanisms such as barbs, interruptions, scales, etc., may be utilized to assist in retention and engagement of the upper and lower shells with the adjacent vertebral body. Upper shell 52 includes tapered leading surface 60 and tapered trailing surface 62, and lower shell 54 includes tapered leading surface 61 and tapered trailing surface 63. As explained further below, upper shell 52 and lower shell 54 each define a cavity or chamber to receive a portion of spacer 56. In the preferred embodiment, the cavity in each shell is substantially rectangular when viewed in a top plan view.

Referring now to FIGS. 10-14, upper shell 52 will be described in further detail, it being understood that lower shell 54 is similarly configured. The upper bone contacting surface of shell 52 is comprised of three separate regions. The first region is a partially cylindrical first lobe 80 having a first bone contacting surface 64 extending convexly along longitudinal axis 51 and interrupted by three ribs 58. The second region is also a partially cylindrical second lobe 82 having a second bone contacting surface 68 that is substantially identical to bone contacting surface 64 extending substantially parallel with surface 64 and convexly along longitudinal axis 51. Second surface 64 is interrupted by three additional ribs 58. In the illustrated embodiment, three such ribs 58 are provided on each convex surface; however, a fewer number or greater number of retention ribs are also contemplated. The third region is an intermediate portion 84 interconnecting the partially cylindrical lobes of the first and second regions. Intermediate portion 84 includes a concave bone contacting surface 66 extending between first bone contacting surface 64 and second bone contacting surface 68.

It will be understood that the combination of surfaces 64, 66, and 68 match a double-barrel insertion sleeve, including those insertion sleeves having a lumen that is figure eight or peanut shaped in cross-section. Implant 50 is placed through the insertion sleeve and into the disc space after reaming the adjacent vertebral end plates to form two substantially cylindrical holes spaced by a desired distance. The distance between the reamed holes in the end plate will determine the size of the intermediate portion 84 between first lobe 80 and second lobe 82. Intermediate portion 84 will be reduced in size as the reamed holes in the disc space are positioned closer to provide the appropriate spacing between convex surfaces 64 and 68. Conversely, as the distance between the reamed holes in the disc space increases, the intermediate portion 84 will be increased in size to provide the appropriate spacing between convex surfaces 64 and 68.

Figure 12:
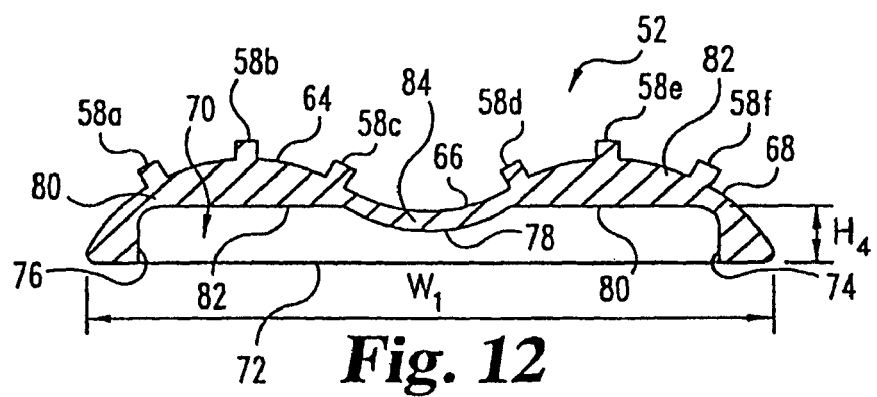
FIGS. 12 and 12*a* are each cross-sectional views of the shell taken along line 12-12 of FIG. 11.
Figure 13:
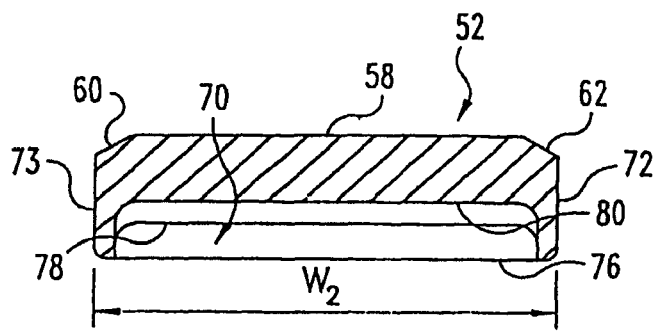
FIG. 13 is a cross-sectional view of the shell taken along line 13-13 of FIG. 11.
Figure 14:
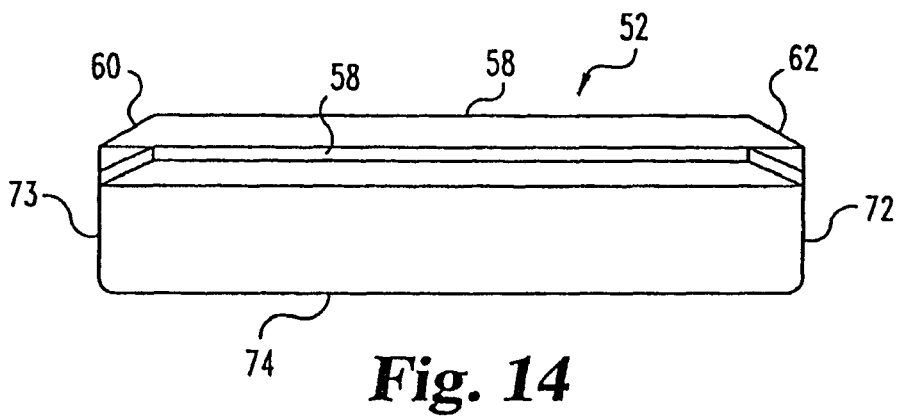
FIG. 14 is a side view of the shell of FIG. 10.

As shown in FIGS. 12-13, spacer retaining cavity 70 is formed by side walls 74 and 76, flat internal load bearing surfaces 80 and 82, a convex arcuate surface 78 extending between load bearing surface 80 and 82, and end walls 72 and 73. In a preferred embodiment, width W1 between side wall 74 and side wall 76 is greater than the width W2 between leading end wall 72 and trailing end wall 73. Cavity 70 has a maximum height H4. Spacer 56 has an upper surface configured for bearing contact with each of the surfaces 80, 82, and 78 in the upper shell 52 and a lower surface to match corresponding cavity bearing surfaces in lower shell 54. As shown more clearly in FIGS. 8 and 9 and as described above with respect to implant 10, greater than fifty percent of the overall height of spacer 56 is unconstrained by the upper and lower shells. Spacer 56 also has opposite sidewalls 69, 71 and opposite endwalls 65, 67 oriented vertically between upper shell 52 and lower shell 54 such that spacer 56 is confined entirely within upper shell 52 and lower shell 54 with no portion of spacer 56 extending outside the sidewalls and end walls of shells 52, 54.

Figure 12A:
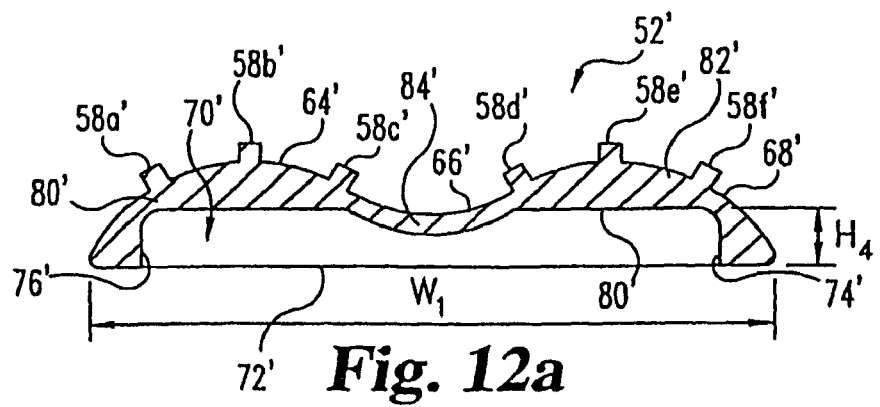

An alternate form of shell 52 is provided in FIG. 12a and designated as 52'. Shell 52' is identical to shell 52, except that cavity 70' is defined by a relatively flat surface 80' extending between leading end wall 72, trailing end wall 73, and sidewalls 74, 76.

Figure 15:
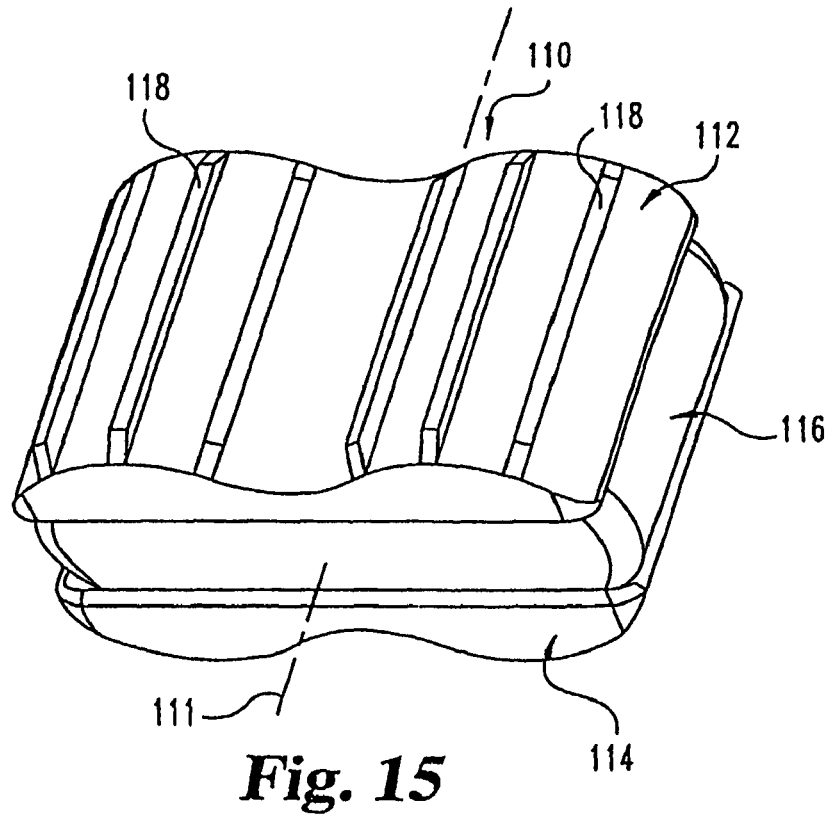
FIG. 15 is a perspective view of still another embodiment of an artificial disc implant according to the present invention.
Figure 16:
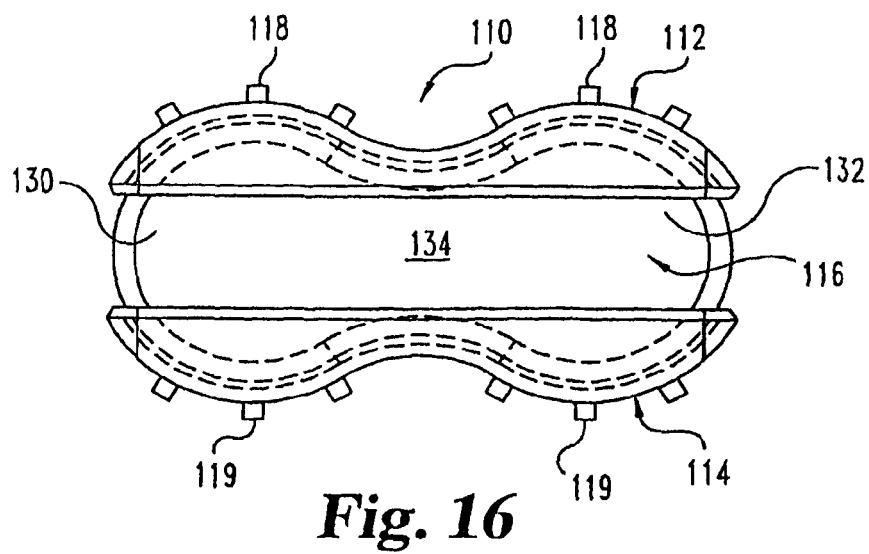
FIG. 16 is an end view of the implant of FIG. 15.
Figure 17:
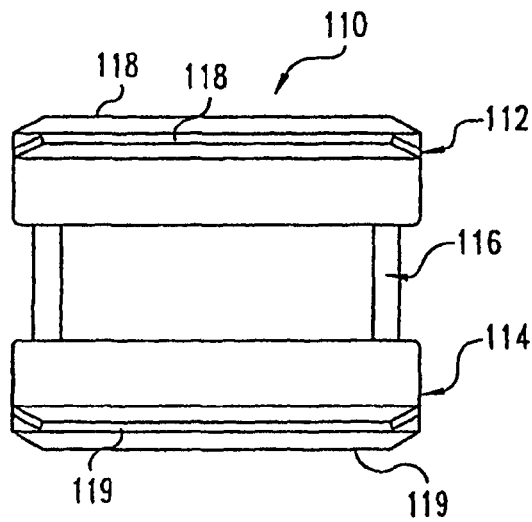
FIG. 17 is a side view of the implant of FIG. 15.
Figure 18:
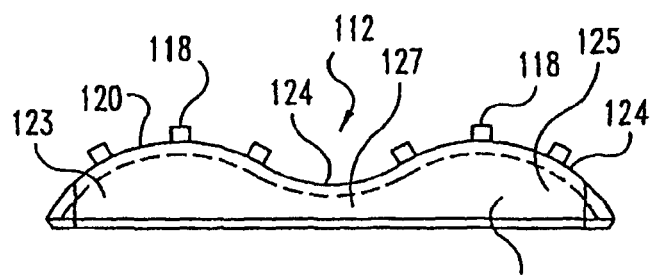
FIG. 18 is an end view of a shell comprising a portion of the implant of FIG. 16.
Figure 19:
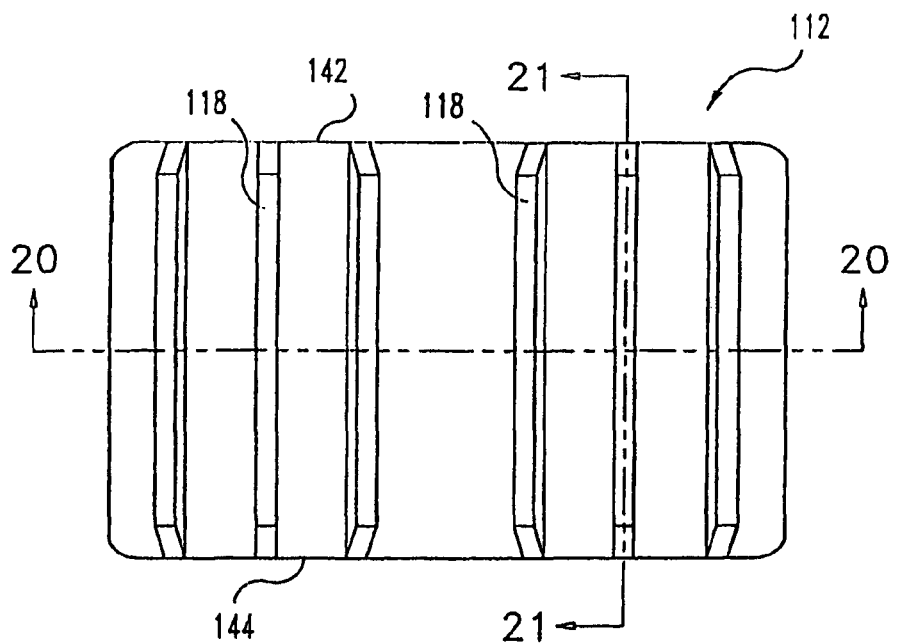
FIG. 19 is a top view of the shell of FIG. 18.
Figure 20:
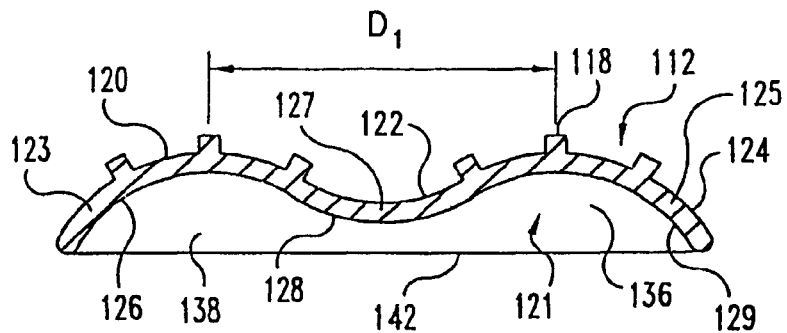
FIG. 20 is a cross-sectional view of the shell taken along line 20-20 of FIG. 19.
Figure 21:
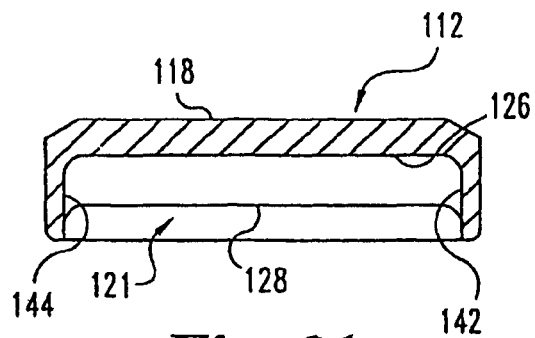
FIG. 21 is a cross-sectional view taken of the shell along line 21-21 of FIG. 19.
Figure 22:
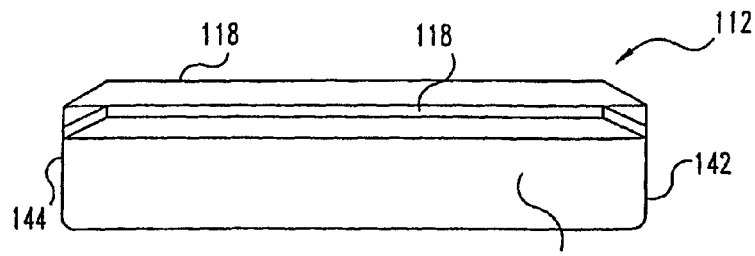
FIG. 22 is a side view of the shell of FIG. 18.
Figure 23:
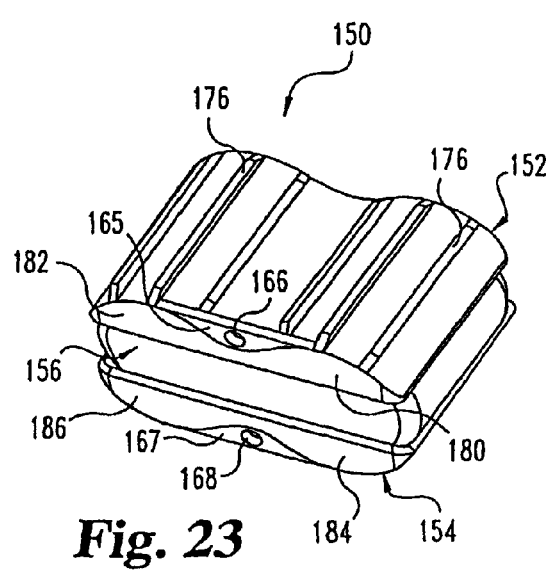
FIG. 23 is a perspective view of a further embodiment of an artificial disc implant according to the present invention.
Figure 24:
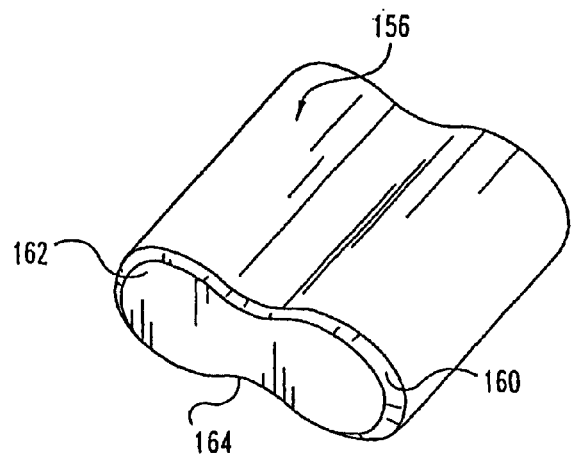
FIG. 24 is a perspective view of a spacer utilized in the implant of FIG. 23.

Referring now to FIGS. 15-17, there is shown yet a further embodiment of an artificial disc implant according to the present invention. Implant 110 includes an upper shell 112, a lower shell 114 separated by a spacer 116. Upper shell 112 includes a number of ribs 118, and lower shell 114 includes a number of ribs 119. The outer configuration of the upper and lower shells 112 and 114 respectively, is substantially identical to the outer configuration of the upper and lower shells 52, 54 of implant 50. Implant 110 differs from implant 50 with respect to the interior cavity adapted to engage spacer 116 and the configuration of spacer 116.

Spacer 116 includes a first substantially cylindrical lobe 130, a second substantially cylindrical lobe 132, and an intermediate portion 134 joining lobes 130 and 132. Preferably spacer 116 is formed as a homogenous unit, and the end view of spacer 116, as shown in FIG. 16, has a substantially figure-eight or peanut shaped configuration.

Referring now further to FIGS. 18-22, there is shown upper shell 112, it being understood that lower shell 114 is substantially identical to upper shell 112, and lower shell 114 will not be further described. Upper shell 112 includes three separate regions. The first region is a first partially cylindrical lobe 123 having a first bone contacting surface 120 extending convexly along longitudinal axis 111 and interrupted by three ribs 118. The second region is a second partially cylindrical lobe 125 having a second bone contacting surface 124 that is substantially identical to bone contacting surface 120. Second bone contacting surface 124 extends substantially parallel with surface 120 and convexly along longitudinal axis 111. Second surface 124 is interrupted by three additional ribs 118. In the illustrated embodiment, three such ribs 118 are provided on each convex bone engaging surface; however, a fewer number or greater number of ribs are also contemplated. The third region is an intermediate portion 127 extending between and interconnecting the first and second cylindrical lobes. Intermediate portion 127 includes a concave bone contacting surface 122 extending between first surface 120 and second surface 124.

Upper shell 112 includes an interior cavity 121 having a first lobe area 136 and a second lobe area 138. Interior cavity 121 is defined by a first interior concave surface 126 extending along and substantially parallel to first bone contacting surface 120, an interior convex surface 128 extending along and substantially parallel to exterior concave surface 122, and a second interior concave surface 129 extending along and substantially parallel to second bone contacting surface 124. Cavity 121 is further bounded by a leading end wall 142 and an opposite trailing end wall 144. Insert 116 is positionable in upper shell 112 and lower shell 114 with first lobe 130 in contact with first interior concave surface 126, second lobe 132 in contact with second interior concave surface 129, and intermediate portion 134 in contact with interior convex surface 128. As previously disclosed with respect to embodiments 10 and 50, the upper and lower shells do not constrain more than fifty percent of the height of spacer 116.

Referring now to FIGS. 23-27, there is shown a further embodiment of an artificial disc implant according to the present invention. Implant 150 includes an upper shell 152, a lower shell 154, and a spacer 156 therebetween. Similar to the spacer 116 of the previously described implant 110, spacer 156 includes a first lobe 160 having a substantially cylindrical configuration, a second lobe 162 having a similar substantially cylindrical configuration, and an intermediate portion 164 joining each of the lobes. As described above with respect to implant 110, the internal cavities of upper shell 152 and lower 154 are adapted to substantially match the configuration of spacer 156. Similarly, shell 152 includes matching cylindrical lobes 180 and 182 interconnected by intermediate portion 181, and lower shell 154 has cylindrical lobes 184 and 186 interconnected by intermediate portion 185. It is further contemplated that implant 150 can have a configuration for spacer 156 and upper and lower shells 152, 154 similar to that described above with respect to implant 50.

Figure 25:
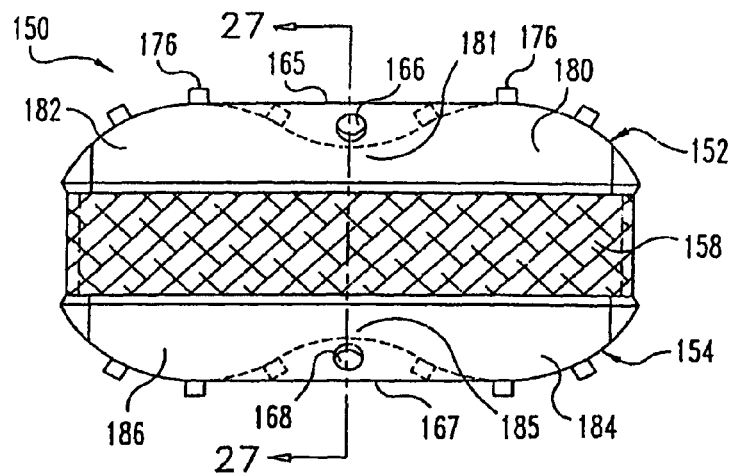
FIG. 25 is an end view of an alternate form of the implant of FIG. 23.
Figure 26:
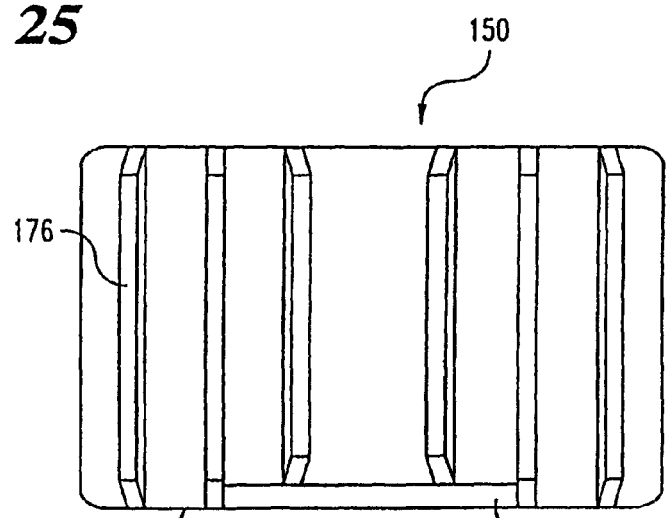
FIG. 26 is a top view of the implant of FIG. 23.
Figure 27:
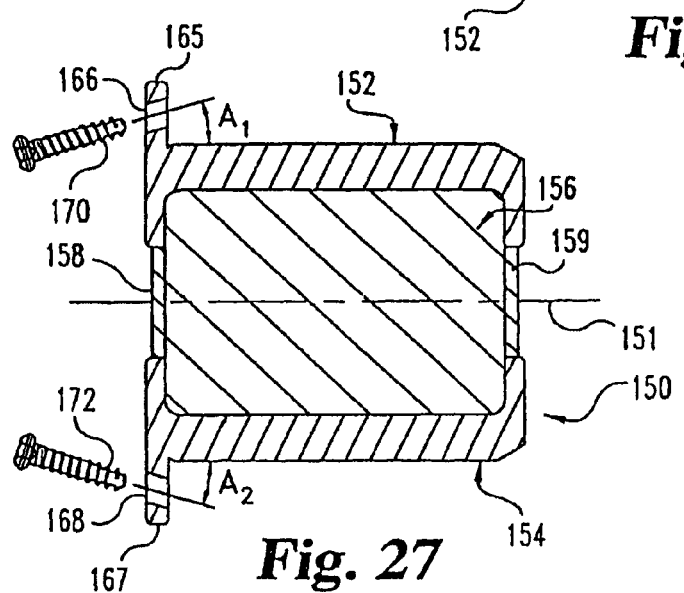
FIG. 27 is a cross-sectional view of the implant taken along line 27-27 of FIG. 25.
Figure 28:
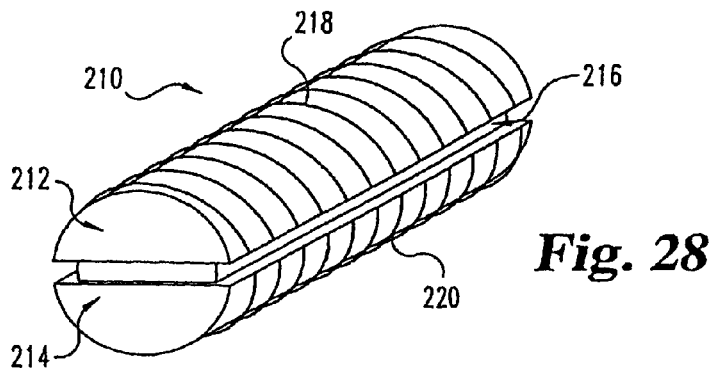
FIG. 28 is a perspective view of another embodiment of an artificial disc implant according to the present invention.
Figure 29:
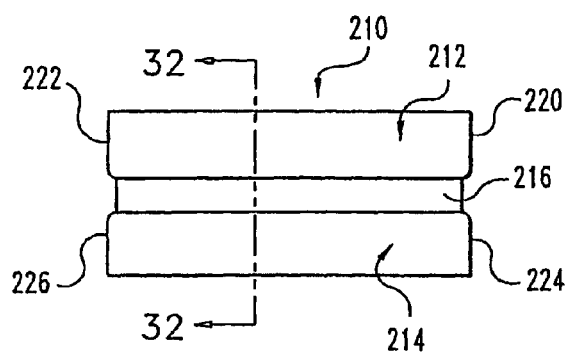
FIG. 29 is a side view of the implant of FIG. 28 with the external thread pattern not shown.
Figure 30:
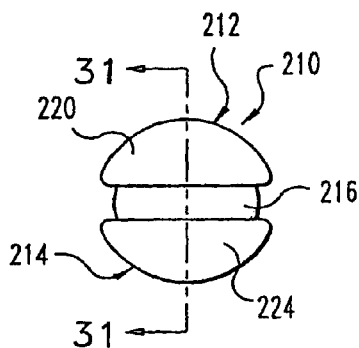
FIG. 30 is an end view of the implant of FIG. 29.
Figure 31:
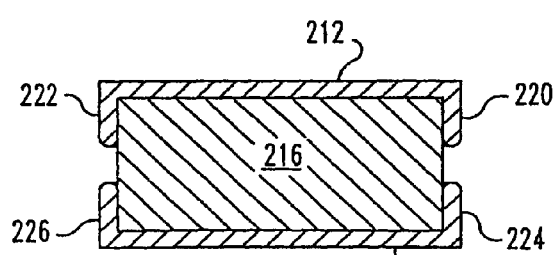
FIG. 31 is a cross-sectional view taken along line 31-31 of FIG. 30.
Figure 32:
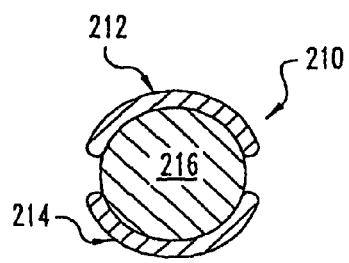
FIG. 32 is a cross-sectional view taken along line 32-32 of FIG. 29.

As shown in FIGS. 25 and 27, implant 150 may further include a flexible membrane 158 extending between and connected to the trailing end walls of upper shell 152 and lower shell 154, and an opposite membrane 159 extending between and connected to the leading end walls of upper shell 152 and lower shell 154. Membranes 158 and 159 may act to limit movement of spacer 156 between the upper and lower shells and expulsion of spacer 156 therefrom. Further, membranes 158 and 159 limit movement of the upper and lower shells with respectively to one another. In a preferred embodiment, membranes 158 and 159 are composed of a braided material. It is contemplated that the braided membranes may be substantially flexible in tension, and outwardly flexible as spacer 156 is compressed. In a further embodiment, a flexible membrane is provided entirely about the spacer between the upper and lower shells.

In another aspect of this embodiment, an upper flange 165 is provided on the trailing end of upper shell 152 extending between lobes 180 and 182. In a similar manner, a lower flange 167 is provided on a trailing end of lower shell 154 extending between lobes 184 and 186. As shown more clearly in FIG. 27, upper flange 165 includes an aperture 166 formed therethrough at an upwardly extending angle A1 with respect to a longitudinal axis 151. A screw 170 is insertable through aperture 166 at angle A1 to threadingly engage the bony structure of the adjacent vertebral body to anchor upper shell 152 thereto. In a similar manner, lower flange 167 has a downwardly extending aperture 168 extending at an angle A2 with respect to longitudinal axis 151. A screw 172 is insertable through aperture 168 to engage the bony structure of the adjacent vertebral body to anchor lower shell 154 thereto.

Referring now to FIGS. 28-32, there is shown an artificial disc implant according to another aspect of the present invention. Implant 210 includes an upper shell 212, a lower shell 214, and a spacer 216 therebetween. Similar to the embodiment shown in FIG. 1, the upper and lower shells are partially cylindrical and the entire implant 210 forms a substantially cylindrical structure. Upper shell 212 includes a thread pattern 218 defined on the outer surface that corresponds and aligns with a similar thread pattern 220 formed on lower shell 214. Thus, implant 210 may be threaded into a disc space with the threads engaging the bony structure of the adjacent vertebrae. Spacer 216 has a cylindrical shape and is formed of an elastomeric compound, more preferably a hydrogel, and is retained within a cylindrical chamber formed by upper and lower shells 212, 214. Upper shell 212 defines a cavity extending between end walls 220 and 222, and lower shell 214 has a cavity extending between end walls 224 and 226. The end walls restrict movement of spacer 216 with respect to upper shell 212 and lower shell 214 and prevent expulsion of spacer 216 therefrom.

Figure 33:
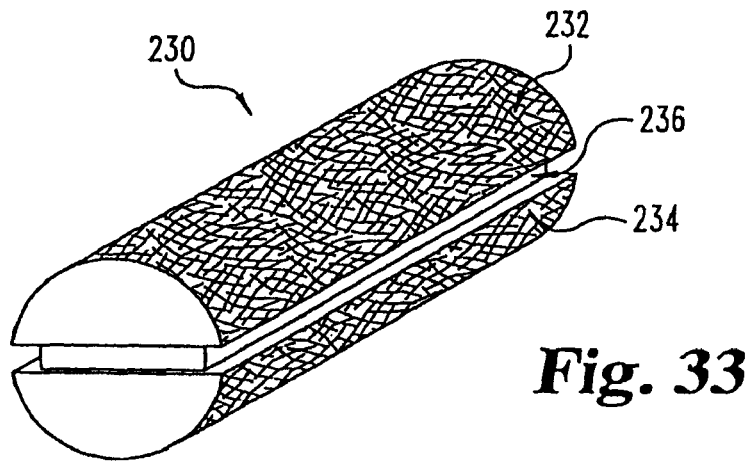
FIG. 33 is a perspective view of a further embodiment artificial disc implant according to the present invention.

Referring now to FIG. 33, there is shown another embodiment of an artificial disc implant according to the present invention. Implant 230 includes an upper shell 232, a lower shell 234, and a spacer 236 therebetween. Implant 230 is substantially cylindrical with the upper and lower shells each defining partially cylindrical portions. The exterior surfaces of upper and lower shells 232, 234 are not uninterrupted with ribs but rather are roughened to create a bone engagement surface. In addition, it is contemplated that the surfaces could be formed such that there may be at least partial bone in-growth into the surface of the shells to assist in anchoring implant 230 in the disc space. The surfaces may further be coated with a BMP substance or other bone growth material to enhance bone growth.

Figure 34:
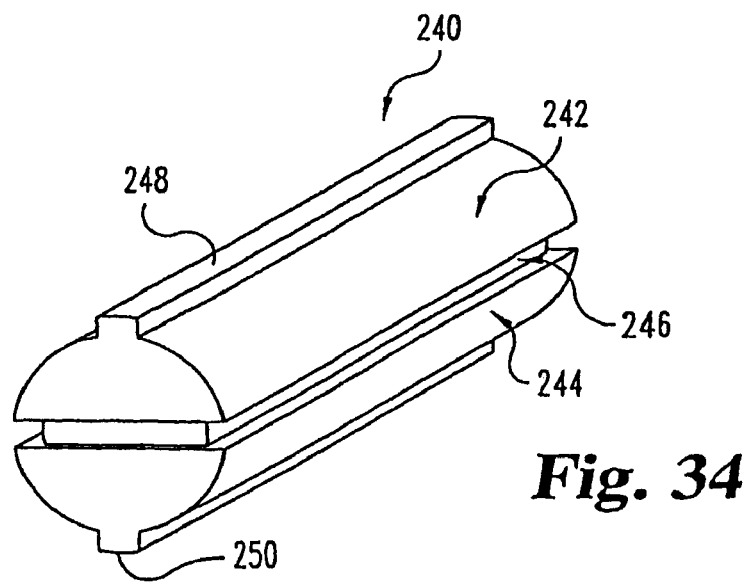
FIG. 34 is a perspective view of yet a further embodiment of an artificial disc implant having a central extension to limit movement in at least one direction.

Referring now to FIG. 34, there is shown another embodiment of an artificial disc implant according to the present invention. Implant 240 includes an upper shell 242, a lower shell 244, and a spacer 246 therebetween. Upper shell 242 includes a single rib 248 extending longitudinally along implant 240, and lower shell 244 includes a corresponding single rib 250, extending longitudinally along implant 240. Ribs 248, 250 engage the bony structure of the adjacent vertebral bodies.

Figure 35:
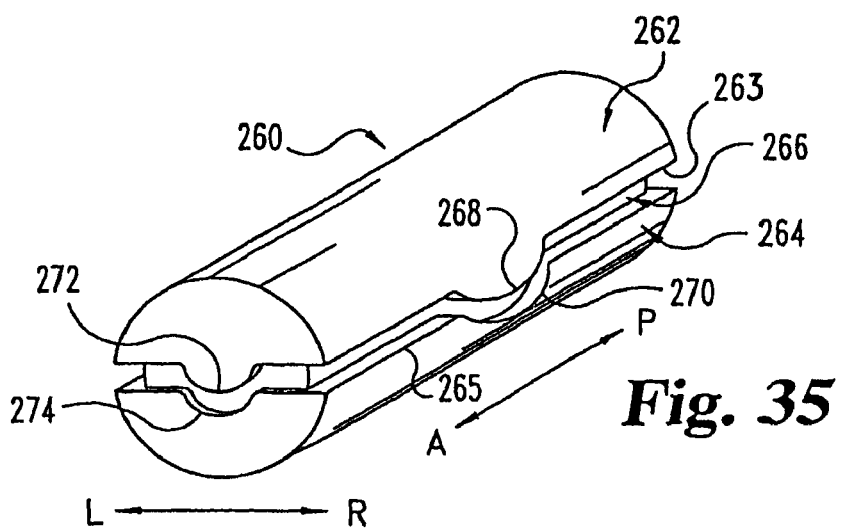
FIG. 35 is a perspective view of still a further embodiment artificial disc implant according to the present invention having a configuration to limit shear forces in the spacer.

Referring now to FIG. 35, there is shown another embodiment of an artificial disc implant according to the present invention. Implant 260 includes an upper shell 262, a lower shell 264, and a spacer 266 therebetween. Upper shell 262 includes a lower edge 263 having a first extension 268 and a second extension 272 extending therefrom towards lower shell 264. Lower shell 264 includes an upper edge 265 having a side wall recess 270 and an end wall recess 272 formed downwardly therein. Recess 270 corresponds to the location of extension 268, and recess 274 corresponds to the location of extension 272. Extensions and recesses may similarly be provided on the end and side of implant 260 not illustrated in FIG. 35. When implant 240 is compressed, positioning of extension 268 in recess 270 will limit movement in the direction of arrows from A to P (anterior to posterior). In a similar fashion, positioning of extension of 272 in recess 274 will limit movement in the direction of arrows L to R (left and right). This limits displacement of the upper and lower shells relative to one another, and also limits shear stresses in spacer 266. While both extensions are shown on upper shell 262, it is contemplated that the combination of extensions and recesses may be alternatively formed in either the upper or lower shells without deviating from the teaching of the present invention. Furthermore, while arcuate recesses and extensions are shown, other configurations and shapes for the recesses and extensions may be utilized, including more closely engaged structures.

Figure 36A:
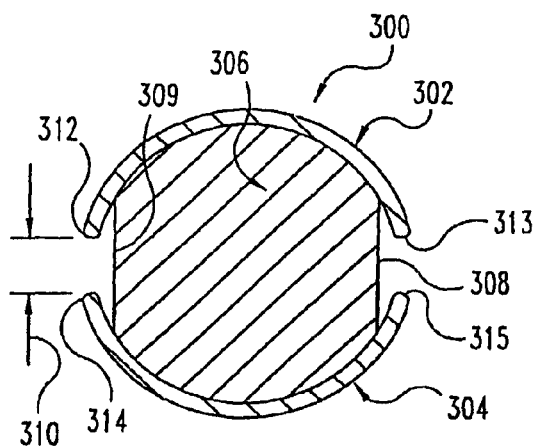
FIG. 36(*a*) is a cross-sectional view similar to FIG. 32 showing an artificial disc implant having a spacer with truncated side walls adjacent the separation between the upper and lower shells.
Figure 36B:
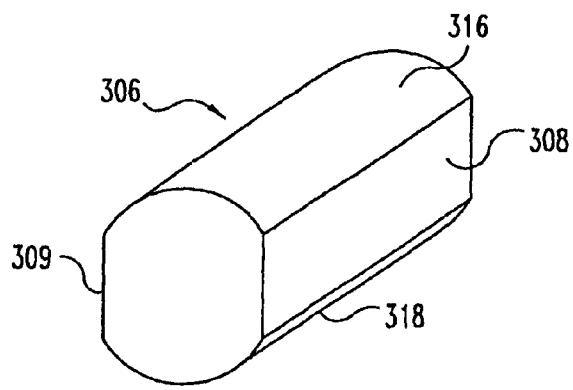
Figure 37:
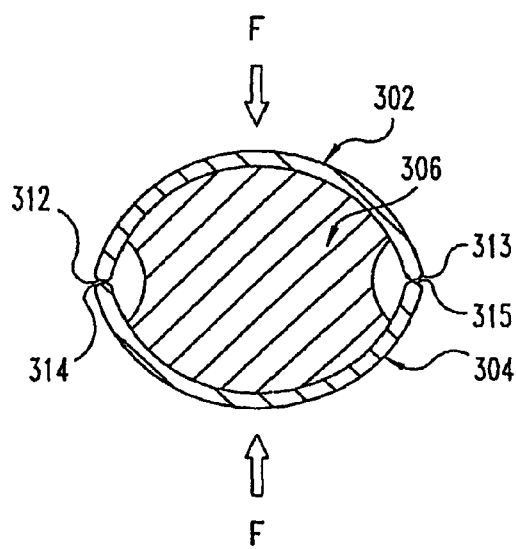
FIG. 37 shows the implant of FIG. 36(*a*) in a compressed state with the truncated side walls compressed to make contact between the upper and lower shells.

Referring now to FIGS. 36a, 36b, and 37, there is shown another embodiment of an implant of the present invention. FIG. 36a shows a cross-section of an artificial disc implant 300 having upper shell 302, lower shell 304, and an intervening spacer 306. As shown in FIG. 36b, spacer 306 includes an upper arcuate surface 316 and a lower arcuate surface 318. The upper and lower arcuate surfaces 316, 318 are adapted to engage the interior arcuate surfaces of upper shell 302 and lower shell 304, respectively. Insert 306 further includes truncated side walls 308 and 309 extending between upper arcuate surface 316 and lower arcuate surface 318. As shown in FIG. 36a, truncated side wall 308 is positioned adjacent the gap between lower edge 313 of upper shell 302 and upper edge. 315 of lower shell 304, and truncated sidewall 309 is positioned adjacent the gap between lower edge 312 of upper shell 302 and upper edge 314 of lower shell 304. These gaps between upper shell 302 and lower shell 304 have a distance 310 when implant 300 is in a relaxed condition and little or no compressive force is applied between the upper and lower shells. As shown in FIG. 37, when significant compressive force F is applied to the upper and lower shells 302 and 304, the edges 313, 315 and the edges 312, 314 come closer together or even into contact, limiting the overall height displacement of implant 300. By providing spacer 306 with truncated side walls 308, 309 pinching of spacer 306 between edges 312, 314 and edges 313, 315 is substantially avoided. Pinching is further limited or prevented by extending the edges of the upper and lower shell laterally beyond the truncated portions of spacer 306.

Figure 38:
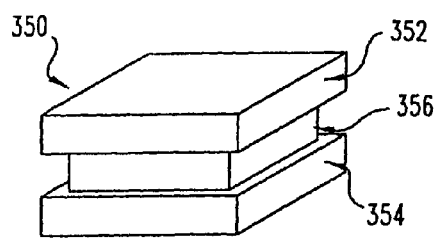
FIG. 38 is another embodiment of an artificial disc implant according to the present invention having a rectangular or square upper and lower shells.
Figure 39:
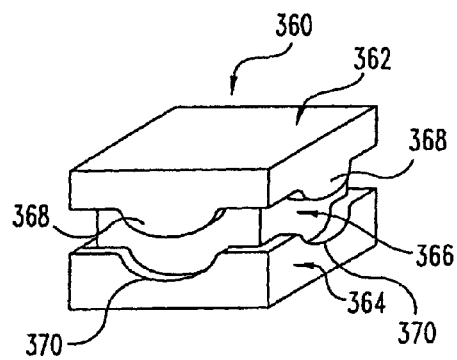
FIG. 39 is the implant of FIG. 38 having upper and lower shells configured to limit shear forces in the spacer.

Reference will now be made to the implants shown in FIGS. 38-41. FIG. 38 illustrates implant 350 having a substantially rectangular or square upper shell 352 and a substantially rectangular or square lower shell 354. A substantially rectangular or square spacer 356 is positioned between upper shell 352 and lower shell 354. In a similar manner, FIG. 39 shows an implant 360 having rectangular or square upper and lower shells 362, 364 and a substantially rectangular or square spacer 366 therebetween. Implant 360 further includes projections 368 extending from upper shell 361, and lower shell 364 includes recesses 370. The recesses 370 receive a corresponding one of the projections 368 as implant 360 is compressed, limiting displacement of the upper and lower shells and the shear forces in spacer 366 as previously described above with respect to implant 260 of FIG. 35.

Figure 40:
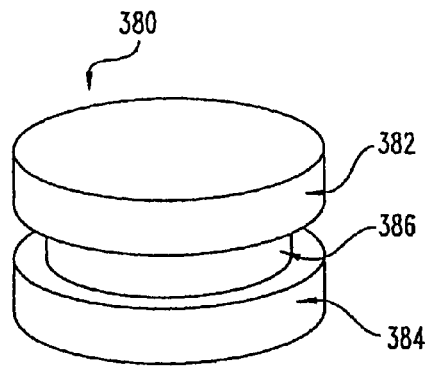
FIG. 40 is another embodiment of an artificial disc implant according to the present invention having substantially circular upper and lower shells.
Figure 41:
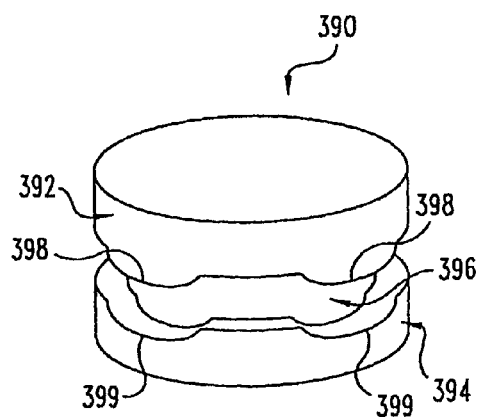
FIG. 41 is the implant of FIG. 40 having upper and lower shells configured to limit shear forces in the spacer.

FIG. 40 discloses a substantially circular implant 380 according to the present invention. Implant 380 includes circular upper shell 382 and circular lower shell 384, and intervening spacer 386 therebetween. In a similar manner, FIG. 41 shows a substantially circular implant 390 having circular upper shell 392 and circular lower shell 394 and a cylindrical spacer 396 therebetween. Implant 390 further includes projections 398 and recesses 399 configured to receive a corresponding one of the projections 398 as implant 390 is compressed. This limits the relative displacement of the upper and lower shells and the shear forces in spacer 396 as previously described above with respect implant 260 of FIG. 35.

Referring now to FIGS. 42 and 43, there is shown a further embodiment of an artificial disc implant of the present invention. FIG. 42 illustrates implant 400 having a partially cylindrical upper shell 402, corresponding lower shell 404, and spacer 406 therebetween. Spacer 406 has a substantially cylindrical shape. Upper shell 402 includes a first lower edge 408 and opposite second lower edge 409. Lower shell 404 includes a first upper edge 410 and opposite upper edge 411. With implant 400 in the relaxed condition shown in FIG. 42, the lower edges and upper edges are spaced by a distance 412. When a force is applied to implant 400 tending to compress it as show in FIG. 43, the lower edges and upper edges become spaced by substantially smaller distance 414. A further feature of implant 400 is that the radius of curvature of spacer 406 is substantially less than a radius of curvature of both upper shell 402 and lower shell 404, and the elastic properties of spacer 406 are selected such that the overall compression of the spacer is limited under the maximum expected load such that distance 414 is the closest the edges of upper shell 402 and lower shell 404 will come toward each other. In this manner, pinching of spacer 406 is prevented.

Referring now to FIGS. 44-45, there is shown yet a further embodiment of an artificial disc implant. Implant 450 includes an upper shell 452, a lower shell 454 and a spacer 456 therebetween. Upper shell 452 includes a bottom surface formed by a series of ridges 458 extending toward lower shell 454. In a similar manner, lower shell 454 includes an upper surface formed by a series of ridges 460 extending toward upper shell 452. The upper and lower surfaces of spacer 456 are likewise ridged to mate with the ridges and valleys formed in the bottom surface of upper shell 452 and the upper surface of lower shell 454. With implant 450 in a relaxed condition shown in FIG. 44, the lower edge 462 of upper shell 452 is spaced from upper edge 464 of lower shell 454 by a distance 466. As the maximum expected compressive force is applied to implant 450, the upper edge 464 and lower edge 462 become spaced by a distance 468 that is substantially less than relaxed distance 466. The elastic properties of spacer 456 are selected such that the overall compression of the spacer is limited under the maximum expected load such that distance 466 is the closest the edges will come toward each other. In this manner, pinching of spacer 406 is prevented.

Utilization of implants according to the present invention will now be further described. It will be understood that access to the disc space, disc removal, and end plate preparation are known in the art and will only be briefly described herein. For example, procedures and instruments useable in a posterior approach to the disc space are disclosed in U.S. patent application Ser. No. 09/179,999, filed Oct. 27, 1998, assigned to the assignee of the present invention, and a publication by Sofamor Danek © 1996 entitled "Surgical Technique using Bone Dowel Instrumentation for Posterior Approach", each of which is incorporated herein by reference in its entirety.

Figure 47:
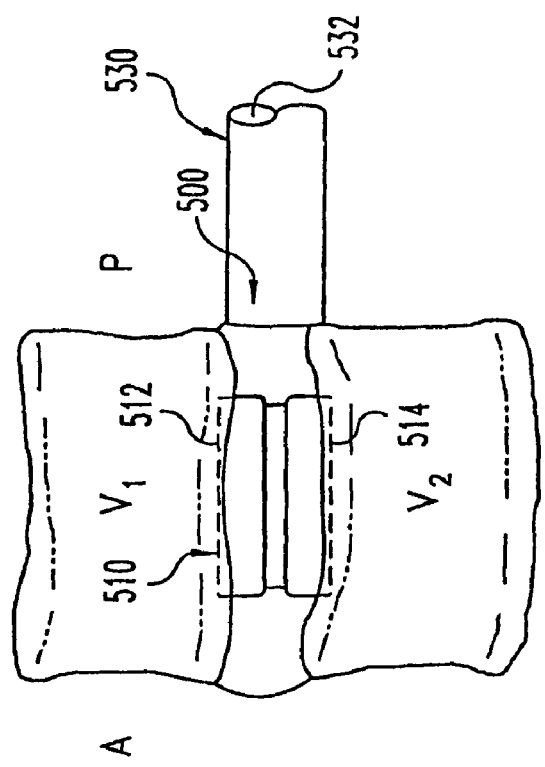
FIG. 47 is a side view of the implants and disc space of FIG. 46.
Figure 46:
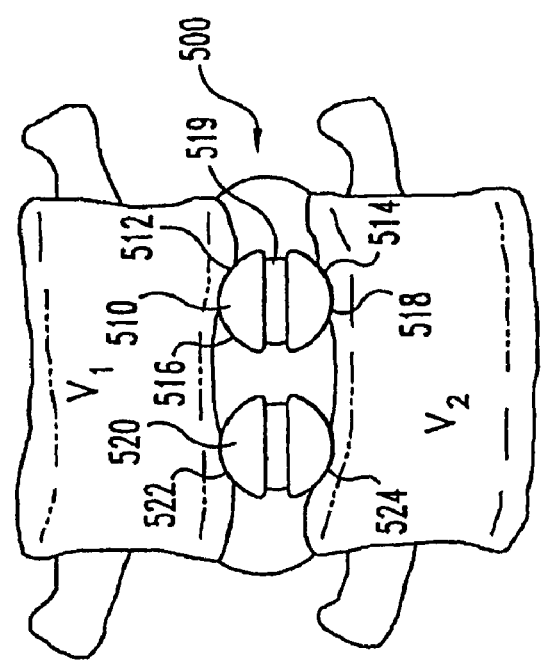
FIG. 46 is an end view showing two of the implants of the present invention inserted into the disc space between two adjacent vertebral bodies.

Referring now to FIGS. 46 and 47, there is shown looking posteriorly a disc space 500 positioned between an upper vertebral body V1 and a lower vertebral body V2. The anterior side of the vertebral bodies is indicated by the letter "A" and the posterior side is indicated by the letter "P". As shown in FIG. 46, two separate implants 510 and 520 are inserted into the disc space, it being understood that implants 510 and 520 can be any of the implant embodiments described herein.

A first implant position may be prepared by removing disc material from disc space 500 and forming, by reaming, cutting, tapping or other technique, arcuate portion 516 in vertebral body Vi. In procedures utilizing an insertion sleeve, such as sleeve 530, a laminectomy or facectomy can also be performed through the sleeve. Similarly, a corresponding and aligned arcuate portion 518 is formed in vertebral body V2. Implant 510 may then be inserted with upper shell 512 contacting and/or engaged in arcuate recess 516, and lower shell 514 contacting and/or engaged in arcuate recess 518. The insertion sleeve 530 can maintain the implant in a reduced-size configuration during insertion through the sleeve by providing sleeve 530 with a channel 532 having a size that is less than the relaxed size of implant 510. The intervening elastic spacer 519 is thereby held securely between the upper vertebral body V1 and the lower vertebral body V2. A similar installation is performed with respect to implant 520 with upper shell 522 securely contacting and/or engaged in upper vertebral body V1 and lower shell 524 contacting and/or engaged in lower vertebral body V2.

Figure 48:
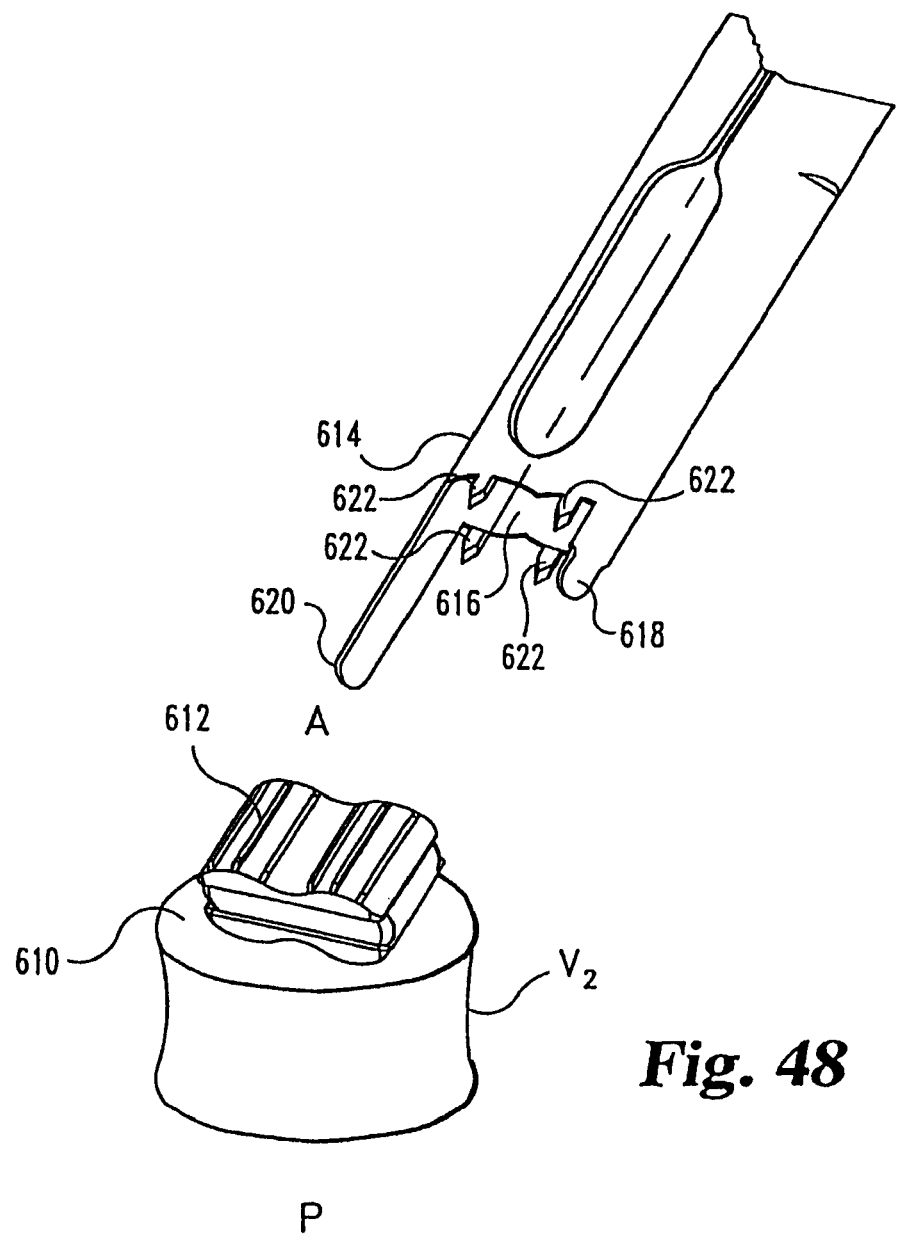
FIG. 48 shows a partial perspective view of a disc space with an implant according to the present invention and being inserted by a substantially lateral approach to a disc space.

As shown in FIG. 47, portions of bony material can remain anteriorly and posteriorly of implant 510 to countersink implant 510 in the disc space and further resist expulsion from the disc space. Such a placement of two separate implants in the disc space as illustrated is more typically performed during procedures that utilize a posterior approach to the disc space. Implants 510 and 520 can also be inserted into the disc space via a posterior approach through single barrel a tube or insertion sleeve 530 via pushing or threading the implants into position through sleeve 530. By inserting two implants in the disc space, each implant will act independently to provide three degrees of motion, while the upper and lower shells protect the spacer from excessive wear or expulsion. Referring now to FIG. 48, there is shown a disc space 610 between vertebral bodies and an implant 612 configured for insertion through a double-barrel insertion sleeve 614. Implant 612 can be any one of the implants 50, 110 or 150 described above. Further, implant 612 can include any structure with a configuration that matches the configuration of interior channel 616 of sleeve 614. The procedure shown in FIG. 48 is performed by an anterior-lateral approach to the disc space 610, although anterior and lateral approaches are contemplated as well. Procedures and instruments useable in an anterior approach are disclosed in U.S. patent application Ser. No. 09/287,917, filed Apr. 7, 1999, assigned to the assignee of the present invention, and a publication by Sofamor Danek © 1996 entitled "Surgical Technique using Bone Dowel Instrumentation for Anterior Approach", each of which is incorporated herein by reference in its entirety. Interior channel 616 of insertion sleeve 614 and implant 612 may be sized such that implant 612 is maintained in an at least partially compressed condition during insertion, allowing insertion of implant 612 into the disc space in a reduced height state. It will be understood that the end plates of the adjacent vertebral bodies to disc space 610 are prepared to receive implant 612 prior to implant insertion. Techniques for shaping the vertebral end plates to conform to the geometry of devices positioned in the disc space are well-known in the art and will not be further described herein. It is preferred that the locations for the cylindrical lobes of implant 612 are prepared by reaming the disc space, and further that the reamed implant location will allow the implant to be countersunk into the vertebral bodies to prevent expulsion of the implant from the disc space. Once implant 612 is inserted, the spacer will expand so that the upper and lower shells contact and/or engage the vertebral endplates to maintain implant 612 in disc space 610.

Referring now to FIGS. 49*a*-51*b*, various implants are shown to accommodate various approaches for inserting the implants into the disc space. For the purposes of clarity the upper and lower shells of the implants are not illustrated in order to more clearly show the orientation and relative sizes of the implant spacers in the disc space. It should be understood that the illustrated spacers could be used with any of the implant embodiments described herein. It should be further understood that the implant spacers may be provided as separate components as shown in FIGS. 49*a*-51*b* or interconnected by an intervening spacer portion extending therebetween.

Referring more specifically to FIG. 49*a*, there is shown an implant 700 inserted via an anterior approach to the disc space. More specifically, it is contemplated an implant inserted with this approach and having this configuration is inserted between the L5 and S1 vertebral bodies, although other vertebral levels are also contemplated. For such an approach, the spacers 702 in implant 700 may have a substantially tapered or truncated trapezoidal shape, as shown in FIG. 49*b*, to establish and/or maintain the appropriate lordosis between the vertebral bodies with the posterior end of the spacer smaller than the anterior end of the spacer.

Referring now to FIG. 50*a*, an anterior-lateral approach to the disc space is taken to insert implant 710 in the disc space. More specifically, it is contemplated an implant inserted with this approach and having this configuration can have particular application between the L4 and L5 vertebral bodies, although other vertebral levels are also contemplated. In this approach implant 710 has an anterior spacer 712 with a substantially tapered or trapezoidal shape, while the posterior spacer 714 has a substantially cylindrical shape, as shown in FIG. 50*b*, to establish and/or maintain the appropriate lordosis between the vertebral bodies.

Referring now to FIG. 51*a*, an implant 720 is positioned in the disc space by a substantially lateral approach. As shown in FIG. 51*b*, implant 720 includes an anterior spacer 722 and a posterior spacer 724. The difference in diameters between insert 722 and 724 is provided to establish and/or maintain the appropriate lordosis between the vertebral bodies. This configuration would be particularly adapted to insertion of implant 720 between vertebral bodies L1 and L5, although insertion at other vertebral levels is also contemplated.

Figure 52:
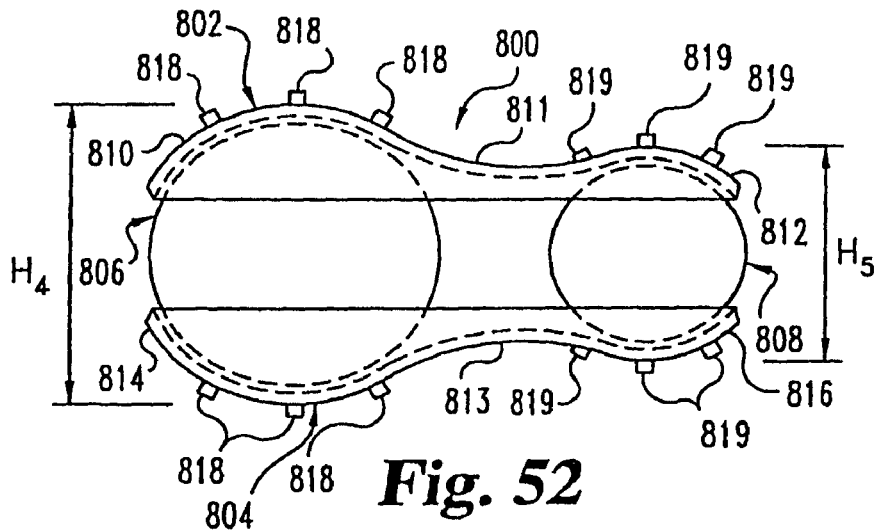
FIG. 52 is an end view of another embodiment artificial disc implant according to the present invention.
Figure 53:
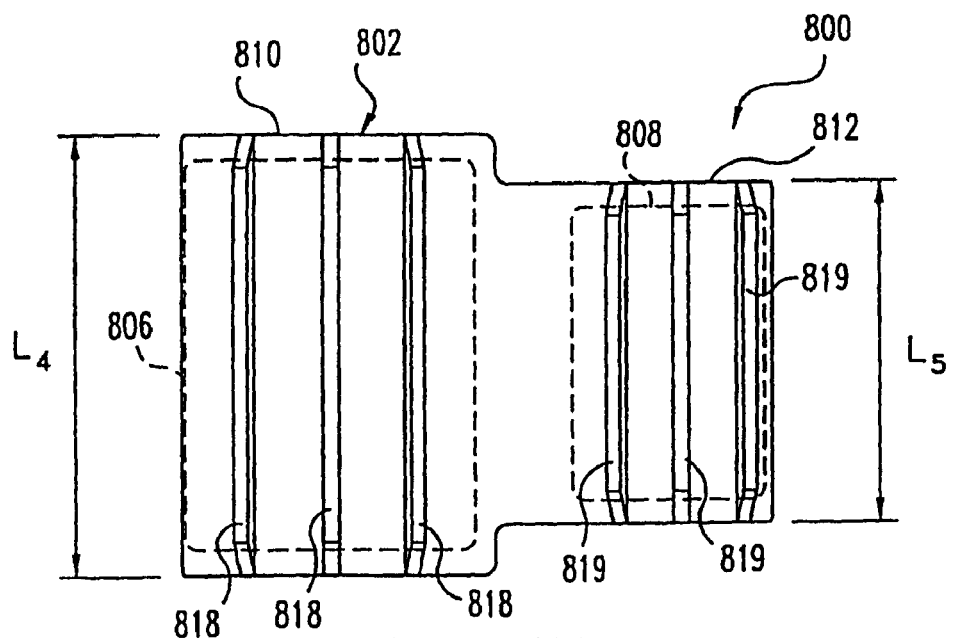
FIG. 53 is a top view of the artificial disc implant of FIG. 52.

Referring now to FIGS. 52 and 53, there is shown a further embodiment of an artificial disc implant of the present invention. Implant 800 includes an upper shell 802 and a lower shell 804. Upper shell 802 includes a first partially cylindrical lobe 810 interconnected with a smaller second partially cylindrical lobe 812 via intermediate portion 811. Lower shell 804 similarly includes a first partially cylindrical lobe 814 interconnected with a smaller second partially cylindrical lobe 816 via intermediate portion 813. Intermediate portions 811, 813 can be provided with varying sizes as needed to achieve the desired spacing between the first and second lobes of shells 802, 804, respectively. A number of ribs 818 extend from first lobes 810, 814 and a number of ribs 819 extend from second lobes 812, 816. A first spacer 806 is positioned between first lobe 810 of upper shell 802 and first lobe 814 of lower shell 804. A second spacer 808 is positioned between second lobe 812 of upper shell 802 and second lobe 816 of lower shell 804.

First spacer 806 has a height H4 that is greater than a height H5 of second spacer 808. First spacer 806 further has a length L4 that is greater than length L5 of second spacer 808. First lobes 810 and 814 are configured to accommodate first spacer 806, and first lobes 810, 814 can be provided with endwalls to prevent spacer 806 from protruding or expulsing therefrom. Second lobes 812 and 816 are configured to accommodate second spacer 808, and second lobes 812, 816 can be provided with endwalls to prevent spacer 808 from protruding or expulsing therefrom. Implant 800 would be particularly suited in a lateral approach to the disc space as discussed above, with first spacer 806 positioned toward the anterior side of the disc space and second spacer 808 positioned towards the posterior side of the disc space. In another embodiment, it is contemplated that an intervening portion may be provided between first spacer 806 and second spacer 808 to connect the first and second spacers forming a single spacer body.

Referring now to FIGS. 54*a*-54*d*, a method for inserting an implant through a double barrel sleeve via a lateral approach to the disc space will now be described. It is contemplated that the method uses double barrel sleeve 612, such as that shown in FIG. 48, to provide an implant insertion path to the disc space. In one specific embodiment, sleeve 612 includes overlapping working channel portions, such as the double barrel sleeve described in pending U.S. patent application Ser. No. 09/498,426, filed Feb. 4, 2000, which is incorporated herein by reference in its entirety. It is further contemplated that the implant inserted according to this technique can be any of the above-described implants, although preferably the implant is one of the embodiments having a pair of interconnected cylindrical lobes. It is further contemplated that aspects of the described techniques also have application with anterior and anterior-lateral approaches.

Figure 54A:
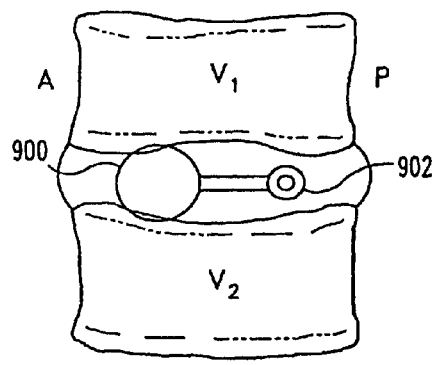
FIGS. 54*a*-54*e* illustrate various steps of a surgical technique according to the present invention.
Figure 54B:
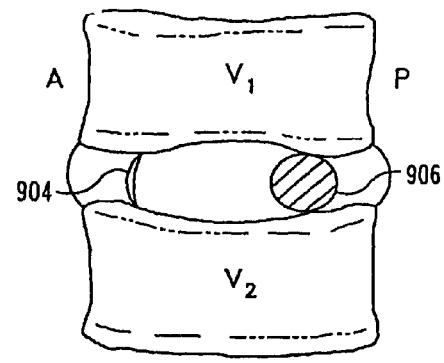

In FIG. 54*a*, a starting point 902 is established with respect to the disc lateral annulus posterior to the midline of the disc. The position of the starting point can be confirmed with a target template fluoroscopically or radiographically. A trephine is inserted to the starting point to incise the disc annulus at the starting point. In FIG. 54*b*, an anterior annulus incision 904 is made vertically in the annulus, and a distraction plug 906 inserted through the starting point incision to distract the disc space to the desired height. In an alternate form, a second distraction plug is inserted anteriorly with respect to distraction plug 906.

Figure 54C:
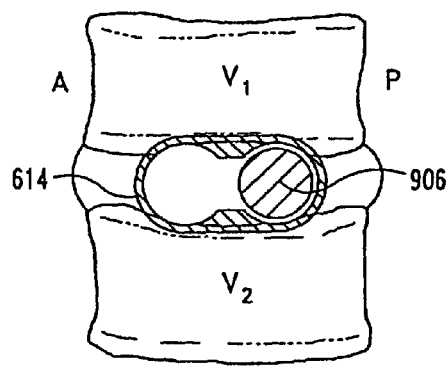

In FIG. 54*c*, double barrel sleeve 614 is inserted over a stem (not shown) extending from distraction plug 906. Preferably, sleeve 614 has tangs 618 and 620 (FIG. 48) that are inserted into the disc space. Preferably, shorter tang 618 is positioned posteriorly and longer tang 620 is positioned anteriorly. It is further contemplated that anterior tang 620 can have a height larger than posterior tang 618 to assist in establishing lordosis. It is further contemplated that the distal end of sleeve 614 can include inferior and superior spikes 622 that can be embedded in inferior vertebra V2 and superior vertebra V1, respectively, to hold the vertebrae at the desired spacing during the procedure.

Figure 54D:
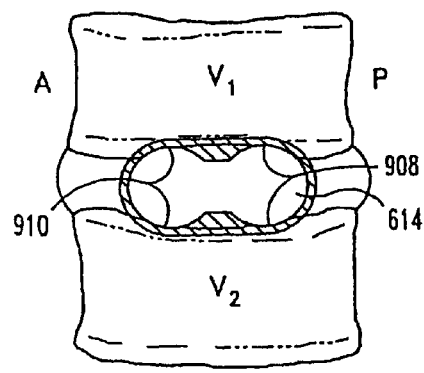

Distraction plug 906 is removed from sleeve 614 and the disc space reamed via a reamer inserted through the respective working channel portions of sleeve 614 to formed posterior reamed location 908 and anterior reamed location 910. If an implant similar to implant 800 is provided, or if separate implants of differing lengths are provided, the disc space is reamed to a greater depth through the anterior working channel portion to accommodate the longer implant portion. When reaming is complete, the reamer is removed, as shown in FIG. 54*d*, and the implant positioned in the working channel of sleeve 614. If necessary, the implant can be compressed from its relaxed state for insertion into working channel 616.

Figure 54E:
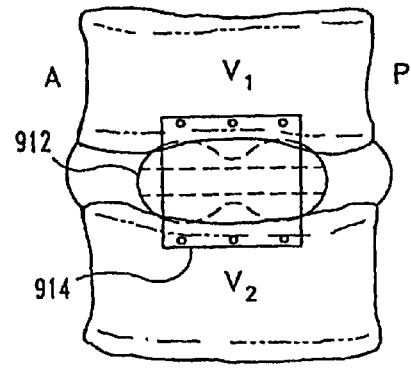

As shown in FIG. 54*e*, implant 912 is pushed through working channel 616 via an impactor and into the disc space. Positioning of the implant in the disc space can be confirmed via fluoroscopic or radiographic instrumentation. When the implant is in the desired position, a braided fabric material 914 can be secured to vertebral bodies V1 and V2 across the entry into the disc space to further resist implant expulsion from the disc space.

The present invention contemplates providing a variety of sizes and shapes of spacers for utilization with upper and lower shells to achieve the necessary angulation between vertebral bodies and to take into account the surgeon's access to the disc space. Further, while the above described combinations have been disclosed herein as being applicable to particular disc space, this is not a limitation on the use of such devices and uses in other manners or other disc space is contemplated as being within the spirit of the present invention.

While the invention has been illustrated and described in detail in the drawings and foregoing description, the same is to be considered as illustrative and not restrictive in character; it being understood that only the preferred embodiments have been shown and described and that all changes and modifications that come within the spirit of the invention are desired to be protected.

What is claimed is:

1. An artificial disc implant system comprising:
a first implant including a first helically threaded upper shell with curved outer and inner surfaces, a first helically threaded lower shell with curved outer and inner surfaces, and a first compressible spacer with a curved upper surface and a curved lower surface, wherein the curved upper surface of the first compressible spacer is movably engaged with the inner surface of the first upper shell and the curved lower surface of the first compressible spacer is movably engaged with the inner surface of the first lower shell such that the first upper shell is spaced apart from the first lower shell, and the threads on the first upper shell are aligned with the threads on the first lower shell when the first compressible spacer is engaged with the first upper shell and the first lower shell; and
a second implant including a second helically threaded upper shell with curved outer and inner surfaces, a second helically threaded lower shell with curved outer and inner surfaces, and a second compressible spacer with a curved upper surface and a curved lower surface, wherein the curved upper surface of the second compressible spacer is movably engaged with the inner surface of the first upper shell and the curved lower surface of the second compressible spacer is movably engaged with the inner surface of the first lower shell such that the second upper shell is spaced apart from the second lower shell, and the threads on the second upper shell are aligned with the threads on the second lower shell when the second compressible spacer is engaged with the second upper shell and the second lower shell,
wherein the first and second implants are sized for side by side and separated placement within an intervertebral space and threaded for attachment to bony structures of two adjacent vertebrae.

2. The artificial disc implant system of claim 1 wherein the curved upper and lower surfaces of the first compressible spacer are convexly curved.

3. The artificial disc implant system of claim 1 wherein the inner surfaces of the first upper and lower shells include a concavely curved surface.

4. The artificial disc implant system of claim 1 wherein the curved outer surfaces of the first upper shell and the curved outer surfaces of the second upper shell each include at least one rib extending outwardly from the curved outer surface.

5. The artificial disc implant system of claim 1 wherein the first and second upper shells each include a tapered leading end and a tapered trailing end.

6. The artificial disc implant system of claim 1 further comprising a flexible membrane extending between the first upper and lower shells and enclosing the compressible spacer.

7. The artificial disc implant system of claim 1 wherein the first implant and the second implant are interconnected by an intervening portion extending therebetween.

8. The artificial disc implant of claim 1, wherein the first implant has a height greater than a height of the second implant.

9. The artificial disc implant of claim 1 wherein the first implant is longer than the second implant.

10. The artificial disc implant of claim 1 wherein the first upper shell is separated from the first lower shell when the first compressible spacer is uncompressed.

11. The artificial disc implant of claim 1 wherein the first compressible spacer is unattached to the first upper and lower shells.

12. The artificial disc implant of claim 1 wherein the first compressible spacer is formed from an elastomeric compound.

13. The artificial disc implant of claim 1 wherein the first upper and lower shells are formed of a material more rigid than the first compressible spacer.

* * * * *